United States Patent
Schechter

(10) Patent No.: US 8,465,534 B2
(45) Date of Patent: *Jun. 18, 2013

(54) RADIO-FREQUENCY TISSUE WELDER WITH POLYMER REINFORCEMENT

(76) Inventor: David A. Schechter, Atascadero, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/102,947

(22) Filed: May 6, 2011

(65) Prior Publication Data

US 2011/0213357 A1 Sep. 1, 2011

Related U.S. Application Data

(63) Continuation-in-part of application No. 12/123,808, filed on May 20, 2008, now Pat. No. 7,945,332.

(51) Int. Cl.
*A61N 1/00* (2006.01)

(52) U.S. Cl.
USPC .......................................................... 607/96

(58) Field of Classification Search
USPC .................................................. 607/96–114
See application file for complete search history.

(56) References Cited

U.S. PATENT DOCUMENTS

| | | |
|---|---|---|
| 2,031,682 A | 2/1936 | Wappler et al. |
| 4,043,342 A | 8/1977 | Morrison, Jr. |
| 5,151,102 A | 9/1992 | Kamiyama et al. |
| 5,156,613 A | 10/1992 | Sawyer |
| 5,403,312 A | 4/1995 | Yates et al. |
| 5,688,270 A | 11/1997 | Yates et al. |
| 5,749,895 A | 5/1998 | Sawyer et al. |
| 5,836,874 A * | 11/1998 | Swanson et al. ............... 600/374 |
| 6,024,741 A | 2/2000 | Williamson, IV et al. |
| 6,086,586 A | 7/2000 | Hooven |
| 6,562,037 B2 | 5/2003 | Paton et al. |
| 6,626,901 B1 | 9/2003 | Treat et al. |
| 6,652,521 B2 | 11/2003 | Schulze |
| 6,682,527 B2 | 1/2004 | Strul |
| 6,726,686 B2 | 4/2004 | Buysse et al. |
| 6,743,229 B2 | 6/2004 | Buysse et al. |
| 6,939,364 B1 | 9/2005 | Soltz et al. |
| 7,025,764 B2 | 4/2006 | Paton et al. |
| 7,087,054 B2 | 8/2006 | Truckai et al. |

(Continued)

FOREIGN PATENT DOCUMENTS

JP 2004-209041 7/2004

OTHER PUBLICATIONS

Extended European Search Report for Patent Application No. EP 08755973.8 dated May 24, 2011, 6 pages.

(Continued)

*Primary Examiner* — Scott Getzow
(74) *Attorney, Agent, or Firm* — James A. Sheridan; Sheridan Law, LLC

(57) ABSTRACT

There are disclosed methods and apparatus for attachment and welding of tissue. In an embodiment, the apparatus includes an energy applicator configured to apply energy to generate heat within a target tissue to evaporate water to create dried tissue, and a thermally conductive material disposed adjacent the first tissue contacting surface or the second tissue contacting surface. The thermally conductive material may be configured for direct contact with the target tissue heated by the energy applicator. The thermally conductive material provides a high coefficient of thermal conductivity so as to evenly distribute heat within the targeted tissue area. Other embodiments are also disclosed.

33 Claims, 24 Drawing Sheets

U.S. PATENT DOCUMENTS

| | | | |
|---|---|---|---|
| 7,090,673 | B2 | 8/2006 | Dycus et al. |
| 7,241,296 | B2 | 7/2007 | Buysse et al. |
| 7,491,202 | B2 | 2/2009 | Odom et al. |
| 7,776,037 | B2 | 8/2010 | Odom |
| 7,794,486 | B2 * | 9/2010 | Quincy, III ............... 607/114 |
| 7,945,332 | B2 | 5/2011 | Schechter |
| 2007/0173872 | A1 * | 7/2007 | Neuenfeldt ............... 606/169 |
| 2008/0033421 | A1 * | 2/2008 | Davis et al. ............... 606/28 |
| 2008/0243213 | A1 * | 10/2008 | Takashino et al. ............ 607/115 |

OTHER PUBLICATIONS

Santini, Mario, et al., "Use of an Electrothermal Bipolar Tissue Sealing System in Lung Surgery", European Journal of Cardio-Thoracic Surgery, vol. 29, pp. 226-230, 2006.

Shigemura, Norihisa, et al., "A New Tissue-Sealing Technique Using the LigaSure System for Nonanatomical Pulmonary Resection: Preliminary Results of Sutureless and Strapleless Thoracoscopic Surgery", New Technology, vol. 77, pp. 1415-1419, 2004.

Tirabassi, Michael V., et al., "Quantitation of Lung Sealing in the Survival Swing Model", Journal of Pediatric Surgery, vol. 39, No. 3, pp. 3870390, Mar. 2004.

Albanese, Craig T., et al., "Experience with 144 Consecutive Pediatric Thoracoscopic Lobectomies", Journal of Laparoendoscopic & Advanced Surgical Techniques, vol. 17, No. 3, pp. 339-341, 2007.

Cano, Indalecio, et al., "Video-Assisted Thoracoscopic Lobectomy in Infants", European Journal of Cardio-Thoracic Surgery, vol. 29, pp. 997-1000, 2006.

Shigemura, Norihisa, et al., "New Operative Method for a Giant Bulla: Sutureless and Stapleless Thoracoscopic Surgery Using the Ligasure System", European Journal of Cardio-Thoracic Surgery, vol. 22, pp. 646-648, 2002.

IPER dated Dec. 3, 2009 for application No. PCT/US2008/064248, 6 pp.

ISR dated Oct. 27, 2008 for application No. PCT/US2008/064248, 3 pp.

* cited by examiner

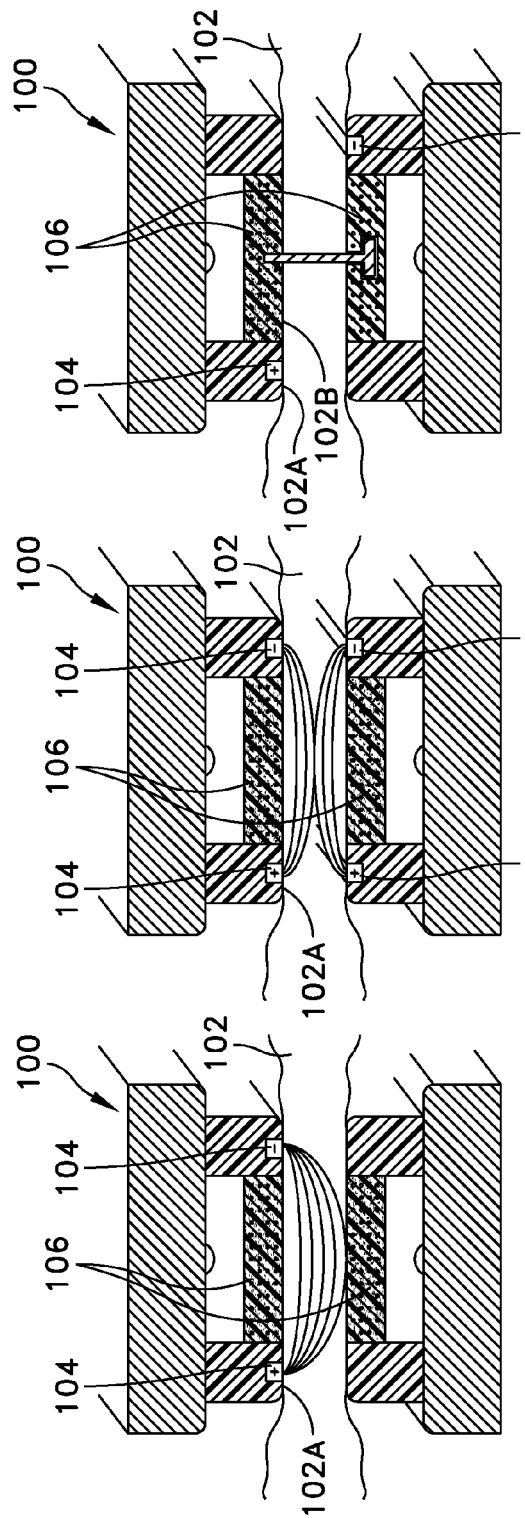
FIGURE 5
FIGURE 4
FIGURE 3
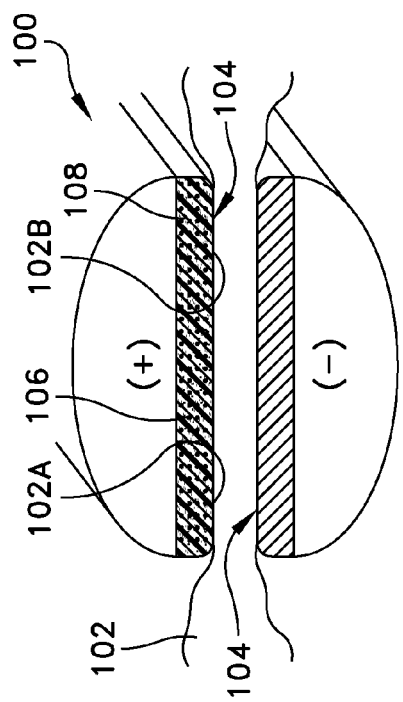
FIGURE 6

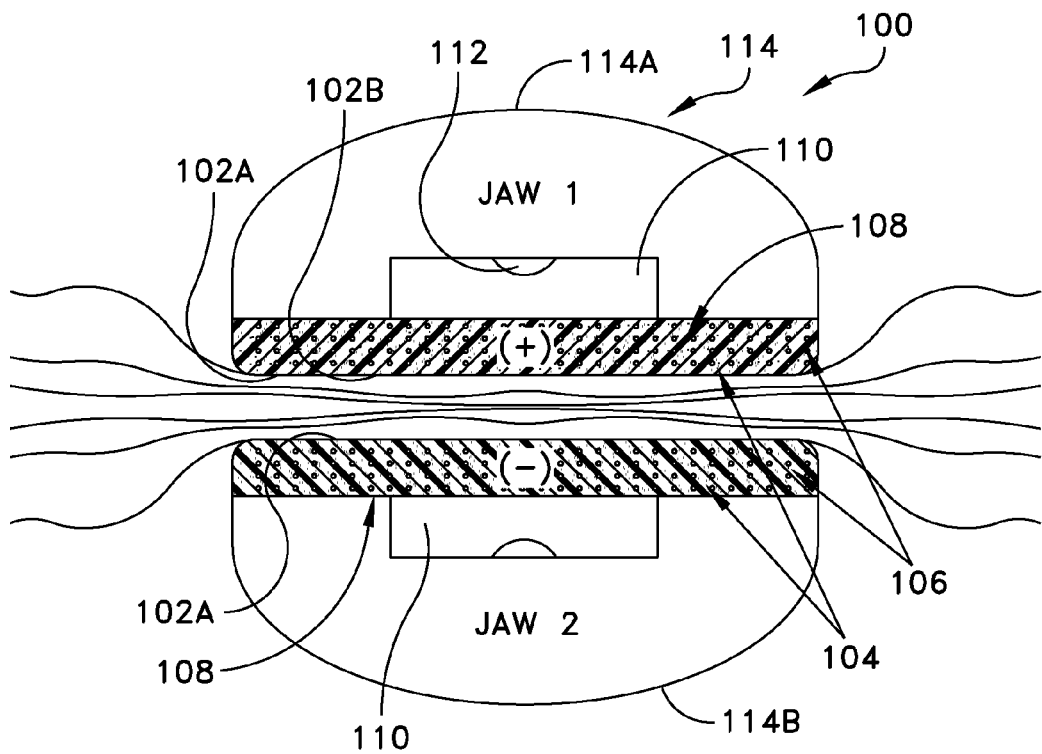
FIGURE 7
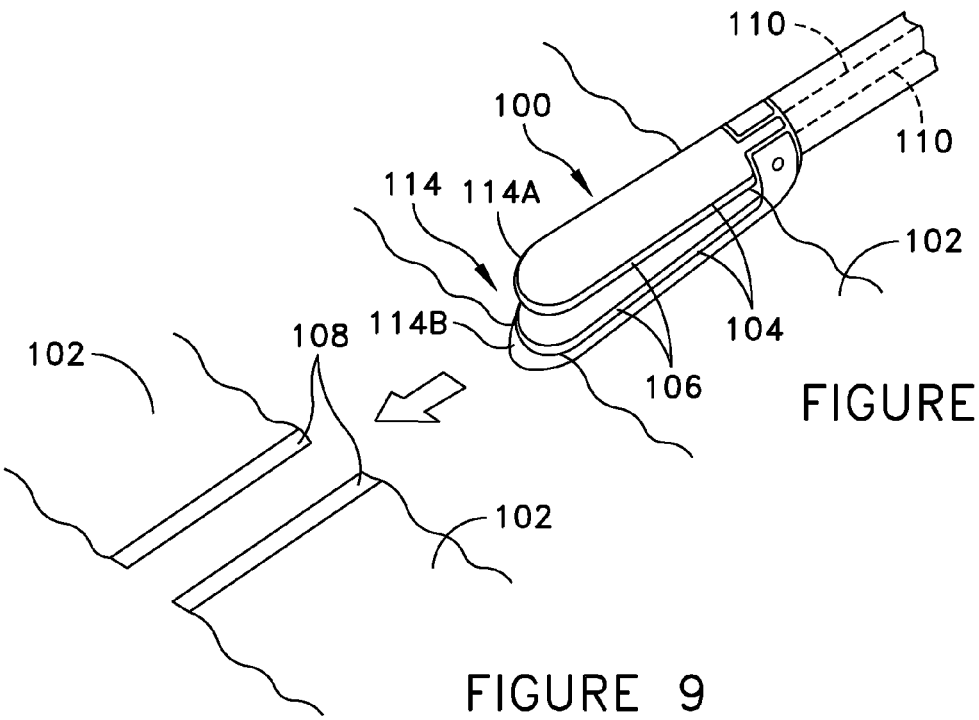
FIGURE 8
FIGURE 9

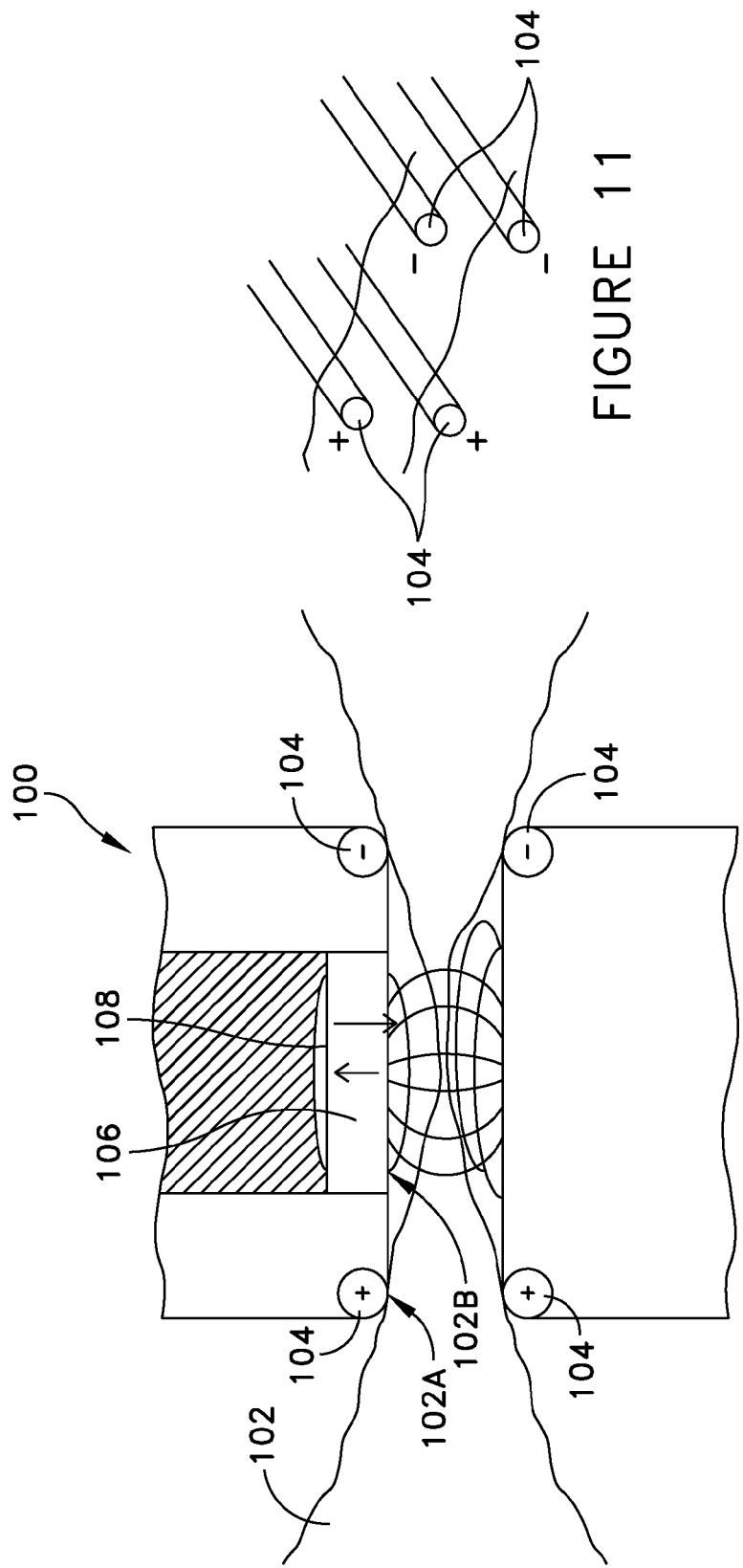

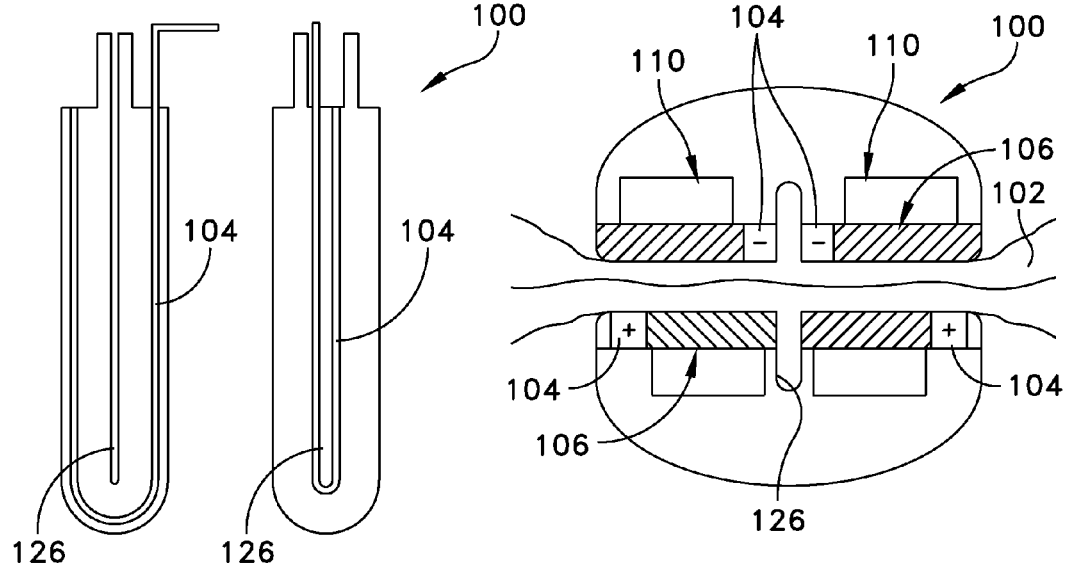
FIGURE 18
FIGURE 19
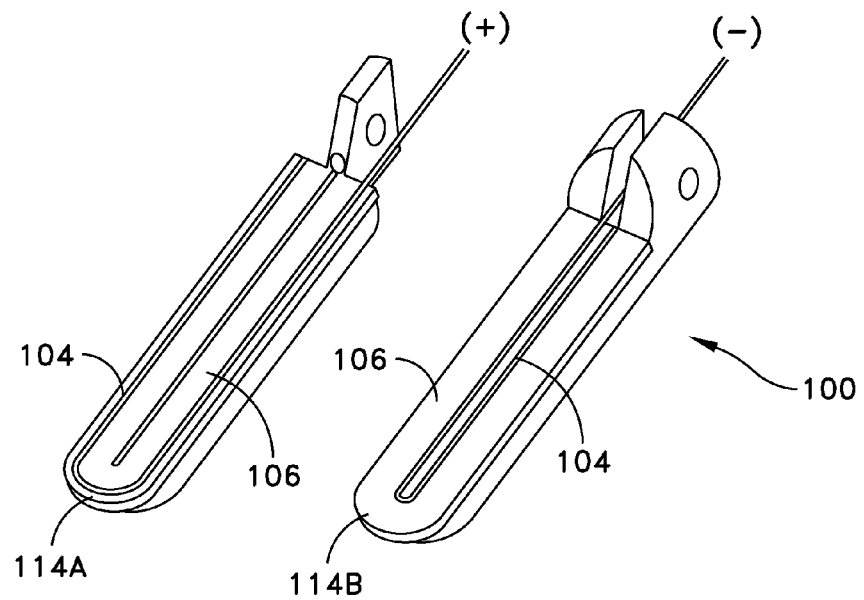
FIGURE 20

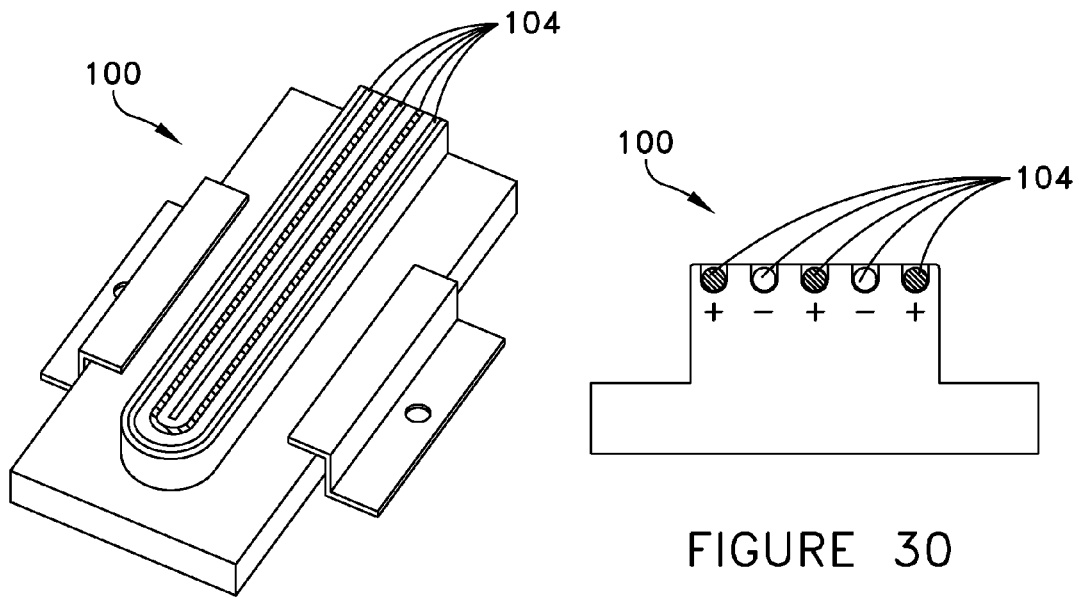
FIGURE 29
FIGURE 30
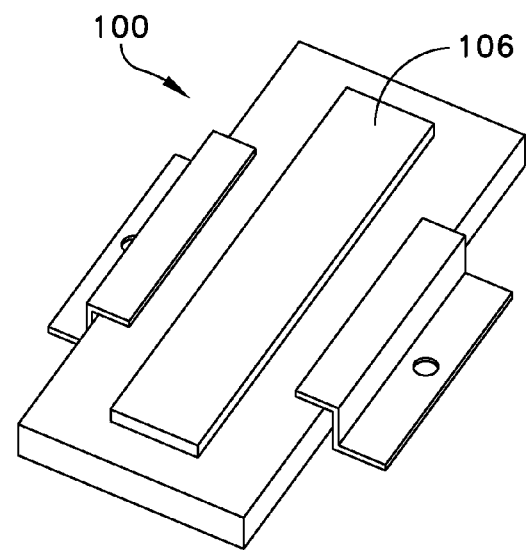
FIGURE 31

RADIO-FREQUENCY TISSUE WELDER WITH POLYMER REINFORCEMENT

REFERENCE TO PENDING PRIOR PATENT APPLICATION

This application claims the benefit of U.S. patent application Ser. No. 12/123,808, filed May 20, 2008 by David A. Schechter for APPARATUS FOR ATTACHMENT AND REINFORCEMENT OF TISSUE, APPARATUS FOR REINFORCEMENT OF TISSUE, METHODS OF ATTACHING AND REINFORCING TISSUE, AND METHODS OF REINFORCING TISSUE, which patent application is hereby incorporated herein by reference.

BACKGROUND

Energy-based tissue welding has previously been used with laser, ultrasonic, radio-frequency (RF) energy, or direct thermal cautery technologies. RF tissue welding and other energy based technologies are commercially available to seal and ligate small blood vessels. Some examples include the LigaSure™ ligation device manufactured by Covidien of Mansfield, Mass., the EnSeal® ligation device manufactured by SurgRx® of Redwood City, Calif., the PKS Seal™ device manufactured by Gyrus Group PLC (Olympus of Toyko, Japan) and the Starion™ ligation device manufactured by Starion Instruments of Sunnyvale, Calif. While these devices are indicated solely for vessel ligation, surgeons have attempted to use available vessel sealing technology to weld large tissue structures such as lung and bowel in thoracic and general surgery.

The primary limitation of adapting currently available vessel sealing technology to large tissue structures is marginal or insufficient weld strength. With current vessel sealing technology, RF energy is directed into the target tissue, which in turn is heated at that location. Electrical current, voltage and power may be adjusted using a closed-loop control algorithm based on feedback variables (e.g., impedance, time, temperature, phase, current, power, and voltage, etc.). The mechanism of fusing tissue in opposite layers relies on collagen and elastin protein denaturation in combination with tissue compression to create a physical entanglement of protein chains. The effected tissue is thermally damaged and non-viable. The acute inflammatory response to the thermal injury is minimal, and the proliferative phase (i.e., fibroblast and collagen deposition) of wound healing is believed to last between 2 to 4 weeks, although strength of the effected tissue can be comparative to native tissue in as little as 7 days.

A significant advantage of RF-energy tissue sealers is the ability to reduce the overall device size as compared to larger mechanical suture devices due to design flexibility with wiring and electrodes. This further enables minimally invasive surgery. The necessity of a smaller endoscopic device has led a number of surgeons to use currently available RF vessel sealing technology on pediatric lung resection and on selected complicated thoracic procedures in adults. (See, for example, Albanese C T, Rothenberg S S. *Experience with 144 consecutive pediatric thoracoscopic lobectomies.* J Laparoendosc Adv Surg Tech A. 2007 Jun.; 17(3):339-41. PMID: 17570785; Rothenberg, S. S., *Thoracoscopy in infants and children: the state of the art*. J Pediatr Surg. 2005 Feb.; 40(2): 303-6. PMID: 15750919; Shigemura N, Akashi A, Nakagiri T. *New operative method for a giant bulla: sutureless and stapleless thoracoscopic surgery using the Ligasure system.* Eur J Cardiothorac Surg. 2002 October; 22(4):646-8. PMID: 12297194; Shigemura N, Akashi A, Nakagiri T, Ohta M, Matsuda H. *A new tissue-sealing technique using the Ligasure system for nonanatomical pulmonary resection: preliminary results of sutureless and stapleless thoracoscopic surgery*. Ann Thorac Surg. 2004 Apr.; 77(4):1415-8; discussion 1419. PMID: 15063276; Tirabassi M V, Banever G T, Tashjian D B, Moriarty K P. *Quantitation of lung sealing in the survival swine model*. J Pediatr Surg. 2004 March; 39(3): 387-90. PMID: 15017557)

For smaller sections, weld strengths on pulmonary tissue are satisfactory and comparable to conventional methods (e.g., surgical staplers). In a study conducted by Tirabassi et al., lung biopsy sites were created with RF energy (using the Ligasure™ ligation device) or an endoscopic stapler (using the Endo-GIA stapler device.) Both biopsy sites had burst strengths equal to or greater than normal lung tissue in the swine survival model after 7 days (84 cm $H_2O$ and 88 cm $H_2O$, respectively.) The wedge biopsy sections had respective average sizes of 0.87 g and 0.78 g. In studies on larger pulmonary resections (e.g., greater than 1.5 grams), the RF vessel sealing weld strength is reduced significantly as demonstrated by Santini et al. (see Table 1).

TABLE 1

Resistance of RF-based wedge resection margins in porcine lungs to the critical pressure of 82 cm $H_2O$ (60 mm Hg) [SANTINI et al.]

| Percentage of RF-based welds with bursts above critical pressure | Resection size (grams) |
|---|---|
| 95 | 0.2 |
| 95 | 0.4 |
| 90 | 0.6 |
| 90 | 0.8 |
| 80 | 1.0 |
| 85 | 1.2 |
| 68 | 1.4 |

Despite the adoption in pediatric thoracic surgery, RF-based tissue welding is generally not used for larger resections, limiting practical use in typical thoracoscopic procedures on adults. Stapling continues to be used for most lung resections. Despite its obvious drawbacks related to size, rigidity, associated complications, and cost, stapling allows simultaneous clamping, severance and closure in adults. However, it may be desirable to increase weld strength and leak resistance in larger resections by reinforcing the weld with a bioabsorbable polymer. Bioabsorbable polymers are currently being used, or investigated for use, in wound closure, scaffolds for tissue engineering, drug delivery systems, cardiovascular, orthopedic, dental, intestinal surgeries, and cosmetic dermatology.

Energy-based tissue welding is currently on the forefront of enabling minimally invasive surgery. Some users have exceeded the limits of existing RF vessel sealing technology for certain types of surgeries. Significant improvements in weld strength may allow larger resections, and may potentially eliminate the need for surgical staples altogether.

SUMMARY OF THE INVENTION

In an embodiment, there is provided apparatus for attachment and welding of tissue, the apparatus comprising an energy applicator positioned adjacent a first tissue contacting surface, the energy applicator configured to apply an amount of energy to generate heat within a target tissue so as to evaporate intracellular and extracellular water from the target tissue to create dried tissue, and denature at least one of collagen and elastin within the target tissue to attach portions of the target tissue together; and a thermally conductive material disposed at a second tissue contacting surface, the thermally conductive material configured for direct contact with the target tissue heated by the energy applicator, and the thermally conductive material providing a path of thermal conduction.

In another embodiment, there is provided apparatus for attachment and welding of tissue, the apparatus comprising an energy applicator positioned adjacent at least one of a first tissue contacting surface and a second tissue contacting surface, the energy applicator configured to apply an amount of energy to generate heat within a target tissue so as to evaporate intracellular and extracellular water from the target tissue to create dried tissue, and denature at least one of collagen and elastin within the target tissue to attach portions of the target tissue together; and electrodes of the energy applicator offset by a distance, the electrodes configured to direct current flow through the compressed tissue in an direction coplanar to the at least one of the first tissue contacting surface and the second tissue contacting surface, and an applied voltage of the energy applicator not exceeding about 100 V(rms)/mm with respect to the offset electrode spacing between the electrodes.

In yet another embodiment, there is provided a method of attaching and reinforcing tissue, the method comprising applying energy adjacent to tissue surfaces with an energy applicator, wherein the application of the energy is configured to generate an amount of heat within a target tissue so as to evaporate intracellular and extracellular water from a target tissue to create dried tissue; and directing contact with the target tissue heated by the energy applicator with a thermally conductive material disposed adjacent the at least one of the first tissue contacting surface and the second tissue contacting surface, and evenly distributing heat within the targeted tissue area with the thermally conductive material providing a high coefficient of thermal conductivity.

In still another embodiment, there is provided method of reinforcing tissue, the method comprising applying energy adjacent a tissue surface with an energy applicator, wherein the application of the energy is configured to generate an amount of heat within a target tissue so as to evaporate intracellular and extracellular water from the target tissue to create dried tissue; and directing current flow through the compressed tissue in an direction coplanar to the at least one of the first tissue contacting surface and the second tissue contacting surface with electrodes of the energy applicator offset by a distance, and limiting an applied voltage of the energy applicator to not exceed about 100 V(rms)/mm with respect to the offset electrode spacing between the electrodes.

Other embodiments are also disclosed.

BRIEF DESCRIPTION OF THE DRAWINGS

Illustrative embodiments of the invention are illustrated in the drawings, in which:

FIGS. 1-8 illustrate various exemplary embodiments of apparatus for attachment and reinforcement, or only reinforcement, of tissue;

FIG. 9 illustrates tissue having reinforced areas with a biopolymer material divided apart using apparatus for reinforcement of tissue;

FIG. 10 is a schematic illustration of apparatus having an radio frequency energy source for attachment and reinforcement of tissue;

FIG. 11 is an illustration of one electrode configuration;

FIGS. 16-24 illustrate embodiments of jaw effectors for attachment and reinforcement of tissue with radio frequency energy sources;

FIGS. 25-32 illustrate various devices having energy applicators and biopolymer applicators for reinforcement of tissue and for creating a hemostatic barrier on adjacent exposed tissue parenchyma on tissues such as liver during resection;

Figure 1:
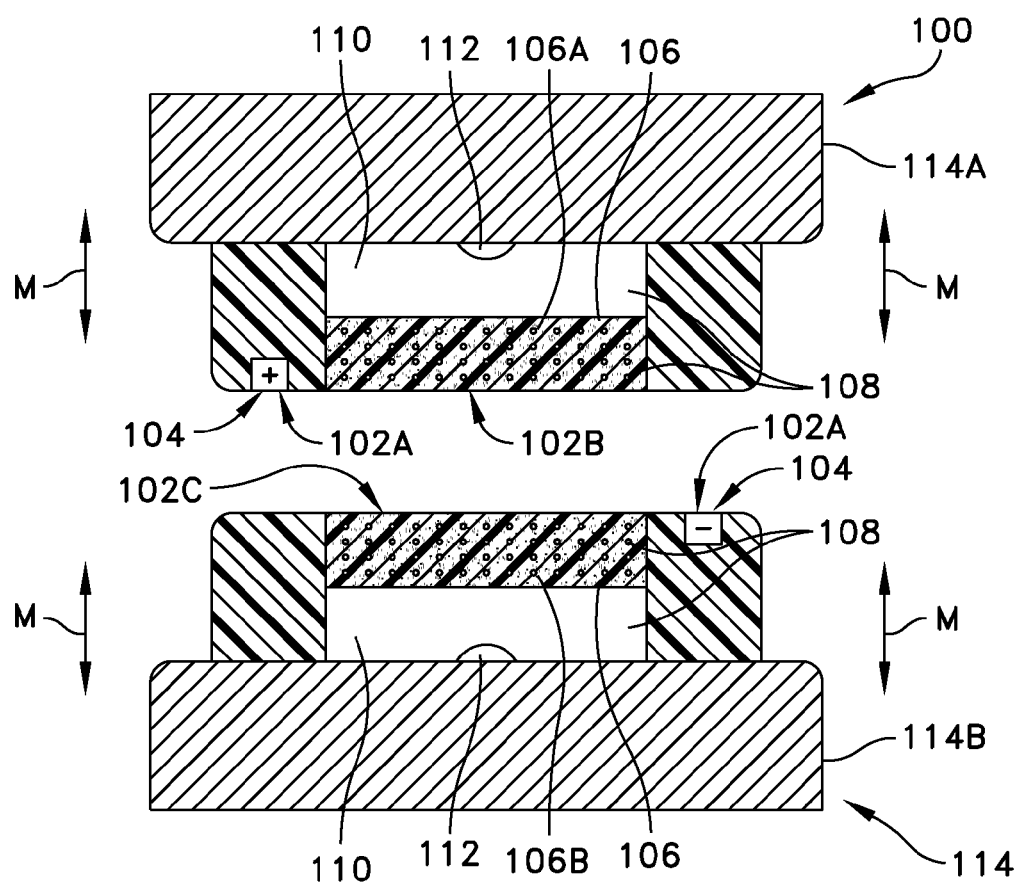

In the following description, reference is made to the accompanying drawings that form a part of the present disclosure, and in which are shown, by way of illustration, specific embodiments of the invention. These embodiments are described in sufficient detail to enable those skilled in the art to practice the invention, and it is to be understood that other embodiments may be utilized and that structural and other changes may be made without departing from the scope of the present invention. The present disclosure is, therefore, not to be taken in a limiting sense. The present disclosure is neither a literal description of all embodiments of the invention nor a listing of features of the invention that must be present in all embodiments.

Numerous embodiments are described in this patent application, and are presented for illustrative purposes only. The described embodiments are not intended to be limiting in any sense. The invention is widely applicable to numerous embodiments, as is readily apparent from the disclosure herein. Those skilled in the art will recognize that the present invention may be practiced with various modifications and alterations. Although particular features of the present invention may be described with reference to one or more particular embodiments or figures, it should be understood that such features are not limited to usage in the one or more particular embodiments or figures with reference to which they are described.

The terms "an embodiment", "embodiment", "embodiments", "the embodiment", "the embodiments", "an embodiment", "some embodiments", and "one embodiment" mean "one or more (but not all) embodiments of the present invention(s)" unless expressly specified otherwise.

The terms "including", "comprising" and variations thereof mean "including but not limited to", unless expressly specified otherwise.

The term "consisting of" and variations thereof mean "including and limited to", unless expressly specified otherwise.

The enumerated listing of items does not imply that any or all of the items are mutually exclusive. The enumerated listing of items does not imply that any or all of the items are collectively exhaustive of anything, unless expressly specified otherwise. The enumerated listing of items does not imply that the items are ordered in any manner according to the order in which they are enumerated.

The terms "a", "an" and "the" mean "one or more", unless expressly specified otherwise.

Headings of sections provided in this patent application and the title of this patent application are for convenience only, and are not to be taken as limiting the disclosure in any way.

DETAILED DESCRIPTION

In an embodiment, a low-molecular weight, bioabsorbable polymer may be introduced to, and penetrate into, thermally denatured collagen and elastin thereby increasing the weld strength. The ability to infuse a low molecular weight polymer and structurally reinforce thermally treated tissue has the potential to enable a vast array of surgical procedures. Efficient infusion of low molecular weight polymers into tissues can be used to improve structural rigidity of tissues, to provide hemostatic barriers, or to physically attach grafts and meshes. Applications of infusion of low molecular weight polymers may range from improving sphincter control in patients with urinary incontinence, reducing blood loss in liver resection, creating rigidity of the uvula in somnoplasty, or improving methods of affixing hernia meshes as well as numerous other applications in cosmetic surgery where bulking is required.

Referring to FIGS. 1-8, there is shown an apparatus 100 for attachment and reinforcement of tissue 102. Apparatus 100 may include an energy applicator 104 positioned adjacent a first tissue contacting surface 102A. Energy applicator 104 may be configured to apply an amount of energy to generate heat within target tissue 102 so as to evaporate intracellular and extracellular water from target tissue 102 to create dried tissue. In an embodiment, apparatus 100 may apply energy to denature at least one of collagen and elastin within target tissue 102 to attach portions of the target tissue together. In one embodiment, the applied energy is configured to denature collagen. In another embodiment, the applied energy is configured to denature both collagen and elastin.

Still referring to FIGS. 1-8, and in an embodiment, a biopolymer applicator 106 may be disposed at a second tissue contacting surface 102B. In one embodiment, surface 102A and surface 102B may be coextensive with one another. In another embodiment, surface 102A and surface 102B may be adjacent to one another on a single portion, such as an end effector, of a device. In an embodiment, surface 102A and surface 102B may be located on separate portions of a device, such as on opposed jaw portions. Biopolymer applicator 106 may be configured for housing a biopolymer material 108 at a location adjacent to the target tissue 102. This allows the biopolymer material 108 to receive the heat generated by the energy applied to target tissue 102 so as to allow biopolymer material 108 to change phase from a solid state to a molten state. This also allows biopolymer material 108 to fill the dried tissue so as to reinforce the portions of target tissue 102 attached to one another and provide a hermetic seal once biopolymer material 108 cools and returns to the solid state.

As heat is generated within tissue 102, it is thermally transferred into porous plate 106 located within a jaw inner face or tissue-contacting region. Porous plate 106 is embedded with biopolymer 108, such that biopolymer 108 is contained within the pores of plate 106. As the porous plate is heated, the biopolymer changes from a solid to a molten state and is drawn or wicked into target tissue 102 by capillary action. The molten low viscosity bioabsorbable polymer 108 fills the voids between the denatured collagen and elastin thereby reinforcing the weld and providing a hermetic seal once the polymer has cooled.

Energy applicator 106 may be configured to provide various types of energy. In an embodiment, energy applicator 106 is a radio-frequency applicator. In another embodiment, energy applicator 106 is a ultrasonic applicator. In one embodiment, energy applicator 106 is a laser applicator. In an embodiment, energy applicator 106 is a microwave applicator. Energy applicator 106 may be configured to emit other types of energy.

Referring again to FIG. 2, biopolymer applicator 106 may include one or more porous plates 106. Porous plate 106 is generally provided to be thermally stable up to a temperature above 200° C. In one embodiment, porous plate 106 is a high temperature thermoplastic. For example, the high temperature thermoplastic may be polytetrafluoroethylene (PTFE). In another embodiment, porous plate 106 is a porous ceramic. In one embodiment, porous plate 106 is a porous metal. The porous metal of porous plate 106 may be configured as an electrode for energy applicator 104 using radio-frequency energy. In an alternative embodiment, porous plate 106 may include a metal surface as an electrode for energy applicator 104 using radio-frequency energy. The symbols (+) and (−) are for reference only and are intended to diagrammatically demonstrate bipolar modes of energy delivery. In another embodiment, energy applicator 104 may use other modes of energy delivery.

Referring now to FIG. 1, and in an embodiment, biopolymer applicator 106 may include a reservoir 110 adjacent to biopolymer material 108 embedded within porous plate 106. Reservoir 110 may containing an additional amount of biopolymer material 108. Reservoir 110 may include a thermal regulator 112, which may be configured to control the change phase of biopolymer material 108 from the solid state to the molten state. Reservoir 110 may include a tube (FIG. 8) along a length of an endoscopic shaft in connection to biopolymer applicator 106.

In another embodiment, porous plate 106 and polymer reservoir 110 may be separately thermally regulated (i.e., heated or cooled). The physical state of biopolymer material 108 may be controlled from a melt to a solid, or vice versa.

In one exemplary embodiment, thermal regulator 112 may include a resistive element to directly heat the biopolymer material and, in turn, control the change phase of biopolymer material 108 from the solid state to the molten state. In another embodiment, thermal regulator 112 may include at least one of a gas heat exchange system and a liquid heat exchange system to thermally regulate biopolymer material 108. Alternatively, thermal regulator 112 may include a thermoelectric cooling system to thermally regulate the biopolymer material. In still another embodiment, thermal regulator 112 may include a direct cooling system to thermally regulate the biopolymer material. Optionally, the direct cooling system may include a saline infusion to thermally regulate biopolymer material 108.

Temperature regulation may provide the ability to thermally regulate reservoir 110, which may be located in a handset portion, and to deliver molten biopolymer material 108 to tissue contacting surface 102B without having to reload polymer or polymer cartridges. This provides the ability to provide a number of consecutive applications.

In one embodiment, reservoir 110 may be configured to actively pump biopolymer material 108 across porous plate 106. In an embodiment, biopolymer cartridges may provide biopolymer material 108. Reservoir 110 may be configured to receive the biopolymer cartridges to provide biopolymer material 108 to biopolymer applicator 106.

Biopolymer material 108 may have many different properties. For example, and in an embodiment, biopolymer material 108 is electrically non-conductive. Biopolymer material 108 may include polycaprolactone (PCL). Biopolymer material 108 may be a polycaprolactone (PCL) copolymer. In one embodiment, biopolymer material 108 may be selected to have one or more properties including, but not limited to, a molecular weight less than 3000 MW, a melt temperature between about 37° C. and 200° C., and a melt viscosity less than about 1000 Centipoise (cps). Alternatively, biopolymer material 108 may have a glass transition temperature of about 60° C. For example, polycaprolactone (PCL) is a very well-studied bioabsorbable, aliphatic polyester with a wide range of physicochemical properties available by copolymerization. Polycaprolactone (PCL) is a semicrystalline polymer with a low glass transition temperature (about 60° C.) Among various bioabsorbable polymers, polycaprolactone (PCL) is relatively hydrophobic and has a very slow degradation rate. In another embodiment, biopolymer material 108 may be a non-bioabsorbable thermoplastic or paraffin wax. The thermoplastic or wax materials may be selected with melt temperatures between 37° C. and 200° C., and melt viscosities less than 1000 centipoise.

Biopolymer material 108 may include a bioabsorbable dye. Visible feedback is provided when biopolymer material 108 with the bioabsorbable dye has been absorbed into target tissue 102. In an embodiment, bioabsorbable dye 108 is methylene blue.

First tissue contact surface 102A and second tissue contacting surface 102B may be adjacent to one another. Alternatively, first tissue contact surface 102A and second tissue contacting surface 102B may be located remotely from one another. For example, first tissue contact surface 102A and second tissue contacting surface 102B of energy applicator 104 may each be positioned on a set of jaws 114. First tissue contact surface 102A and second tissue contacting surface 102B may be adjacent to one another on one jaw 114A or 114B of the set of jaws 114. For apparatus 100 including jaws 114, an example of relative movement is denoted by reference character M in FIG. 1. First tissue contact surface 102A and second tissue contacting surface 102B may be located remotely from one another on opposed jaws 114A, 114 of the set of jaws 114.

Biopolymer applicator 106 may include a third tissue contacting surface 102C. In an embodiment, second tissue contacting surface 102B may include a first porous plate 106A and third tissue contacting surface 102C may include a second porous plate 106B. Second tissue contacting surface 102B and third tissue contacting surface 102C may be located remotely from one another on opposed jaws 114A, 114B of the set of jaws 114.

Figures 2A, 2B, 2C:
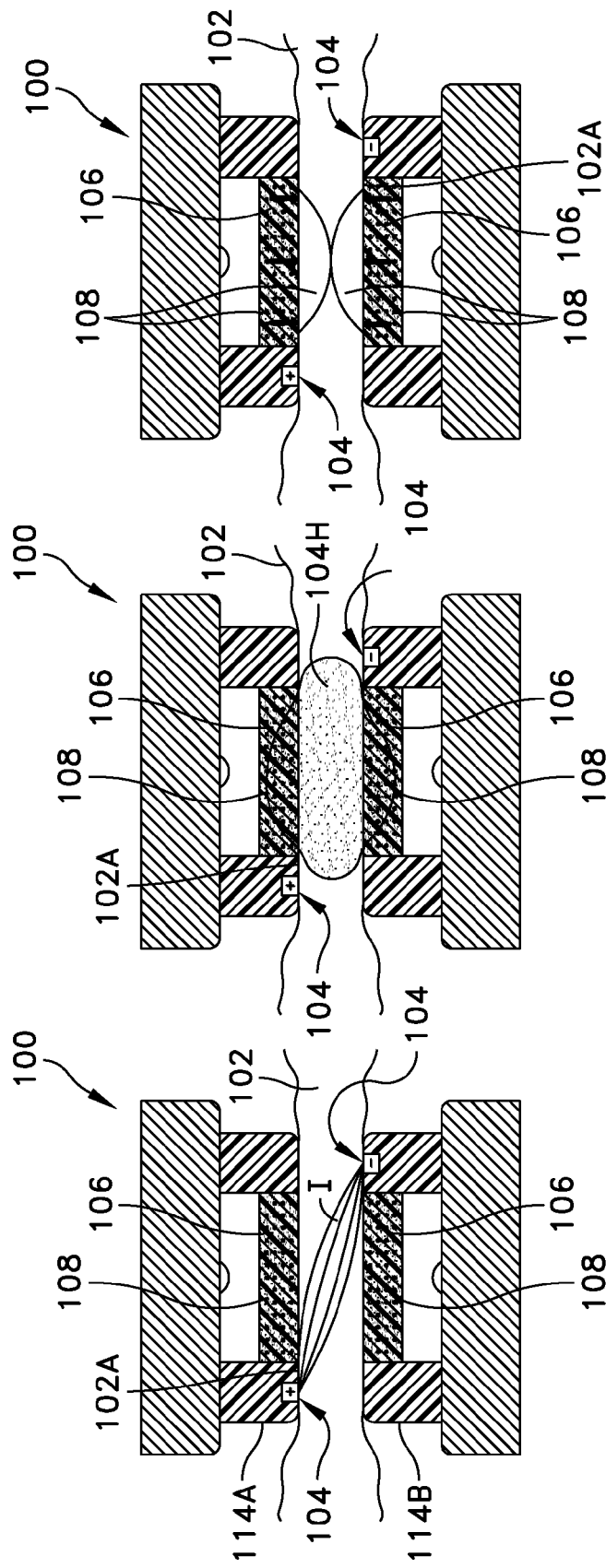
Figure 12:
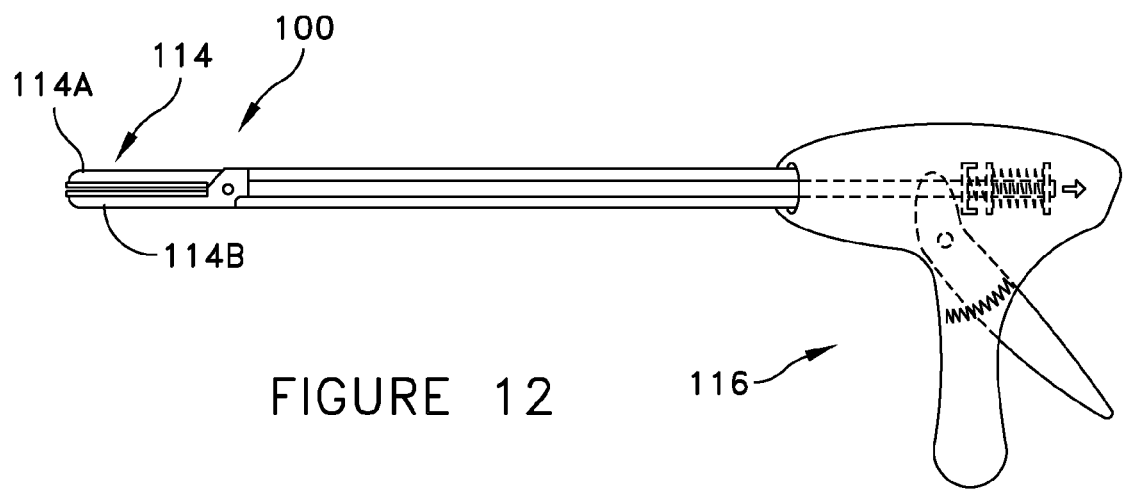
FIGS. 12-15 illustrate various clamping mechanisms for selectively applying pressure to tissue.
Figure 13:
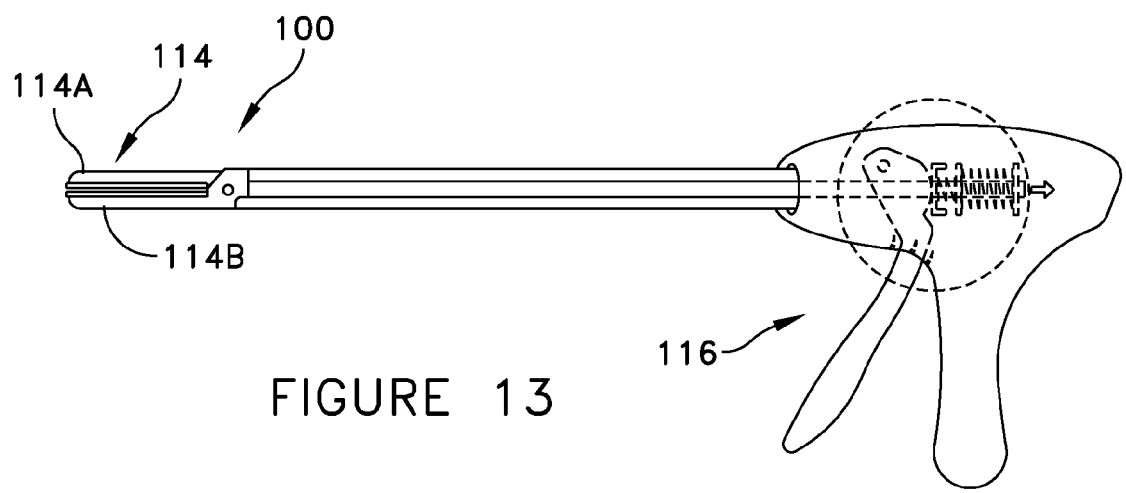
Figure 14:
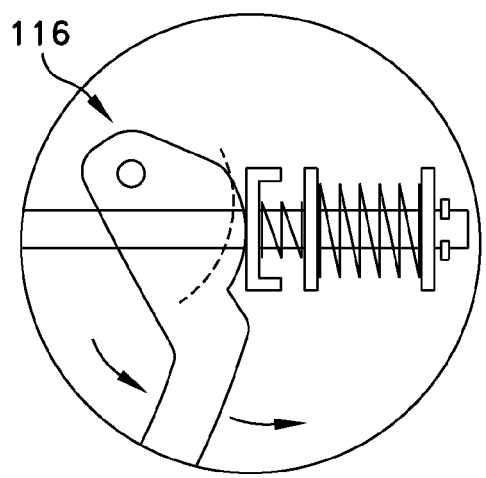

As illustrated in FIGS. 2A-2C, and in an embodiment, porous plate 106 may be electrically non-conductive and located on tissue contacting surface 102A of at least one of the grasping jaws. As illustrated in FIG. 2A, grasping jaws 114 may apply tissue compression force. Porous plate 106 is in direct contact with the heated target tissue, providing a path of thermal conduction into biopolymer 108. Electrodes 104 may be configured such that current (see reference character I in FIG. 2A) flows in a side-to-side (i.e., parallel) manner across the width or length of jaw 114A. This can be achieved using electrodes offset from each other along the width or length of grasping jaw 114, either on the same tissue-contacting surface or on opposing tissue contacting surfaces. Offset is defined as an electrode configuration, where electrodes located one jaw are not geometrically or directly opposed to an electrode of a different potential or polarity located on the corresponding mating jaw. An offset configuration can also exist with electrodes located on only one jaw surface, such that the electrodes of differing electrical potentials are spaced apart with current flowing substantially planar to the clamped tissue (FIG. 3). Additionally, offset configurations can include a plurality of electrode sets (FIG. 4). As shown in FIG. 2B, heat 104H is generated between jaws 114. In FIG. 2C, there is shown biopolymer 108 wicked into tissue 102.

Referring to FIGS. 16-20, and in an embodiment, electrodes 104 are offset and configured as an inner electrode and outer u-shaped ring. The inner electrode 104 and outer electrode 104 are arranged such that the linear distance from one another remains consistent with reference to plane of clamped tissue 104. Outer electrode 104 is located on at least one tissue contacting surface and inner electrode 104 is located on at least one of the tissue contacting surface (FIGS. 18-20.) Both inner and outer electrodes 104 may be disposed on the same tissue contacting surface and the opposing tissue contacting surface corresponding to porous plate 106. This provides simplicity of design and ease of manufacture although functionally the inner and outer electrodes may reside on opposing surfaces and the porous plate may be on one or both tissue contacting surfaces.

In an another embodiment, porous plate 106 is electrically conductive and located on the tissue contacting surface of at least one of the grasping jaws, and may be located on both jaws with each porous plate 106 electrode having opposite polarity (FIG. 7). Electrical current is conducted through porous plate 106 and into tissue 102. As illustrated in FIG. 6, and in one embodiment, only one of jaws 114A, 114B need contain electrically conductive porous plate 106.

Grasping jaws 114 may include pressure controlled clamping of target tissue 102. Jaws 114A, 114B may grasp and approximate tissue with a low pressure or low force to allow for positioning and tissue manipulation with out excessive tissue damage (for example, less than 1 kgf/cm$^2$) and allow for a high pressure clamping for tissue welding (for example, about 5 to 10 kgf/cm$^2$). Alternatively, the grasping mechanism may be designed such that energy can be applied initially at the low pressure set-point and transitioned to the high pressure set-point during activation. This can allow for improved incorporation of elastin into the tissue weld as high pressure may prematurely tear the elastin fibers and weaken the tissue weld.

Figure 15:
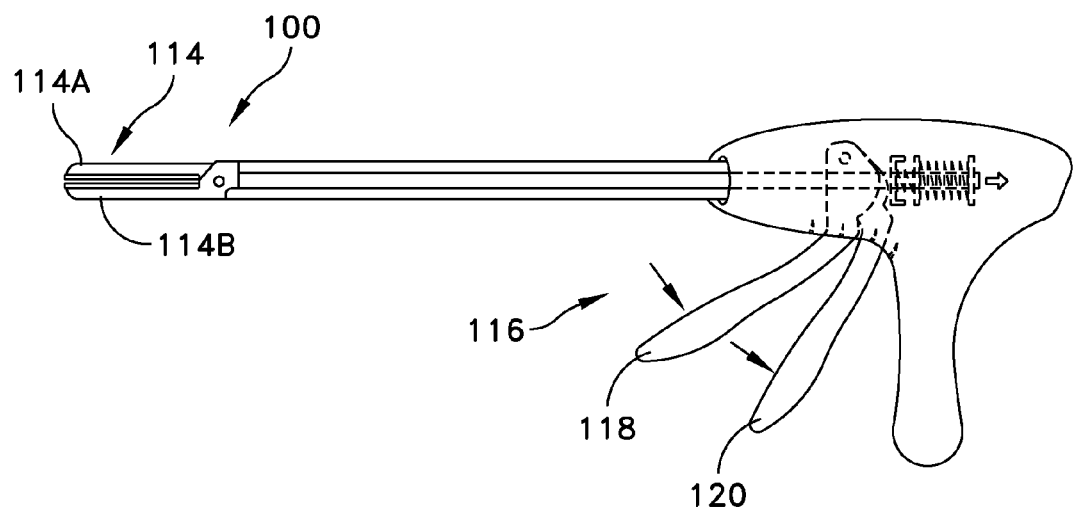
Figure 16:
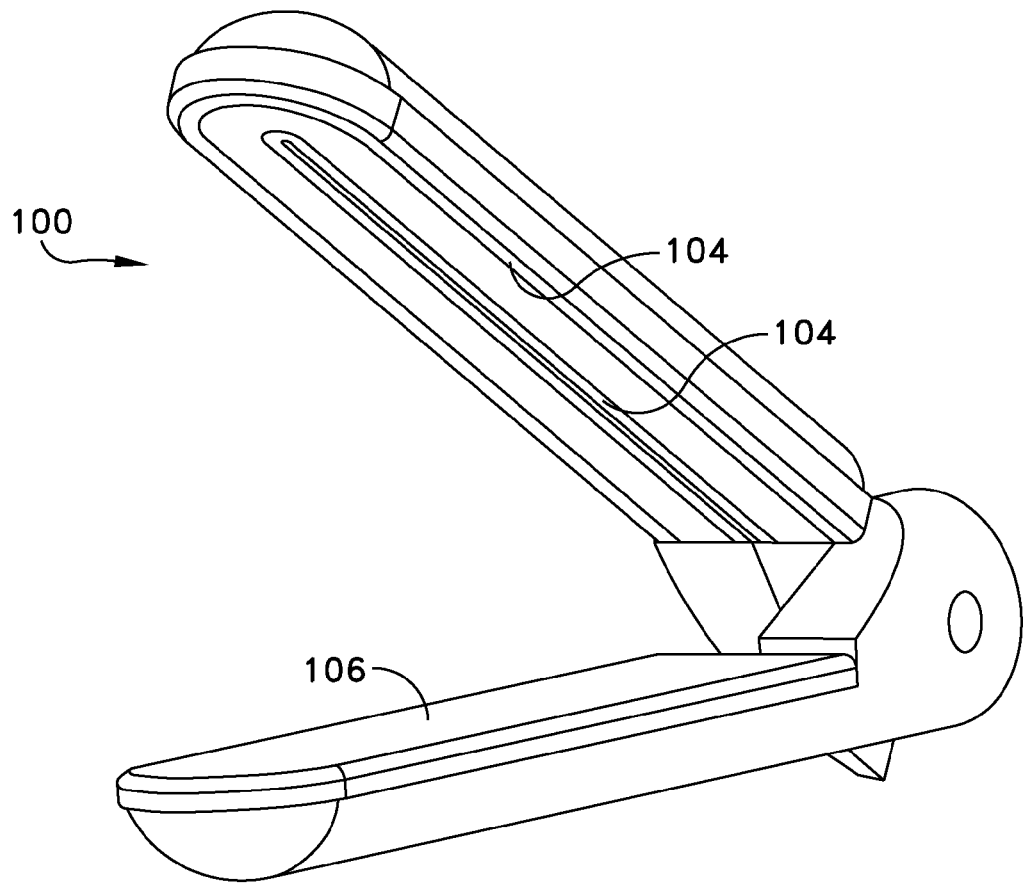
Figure 17:
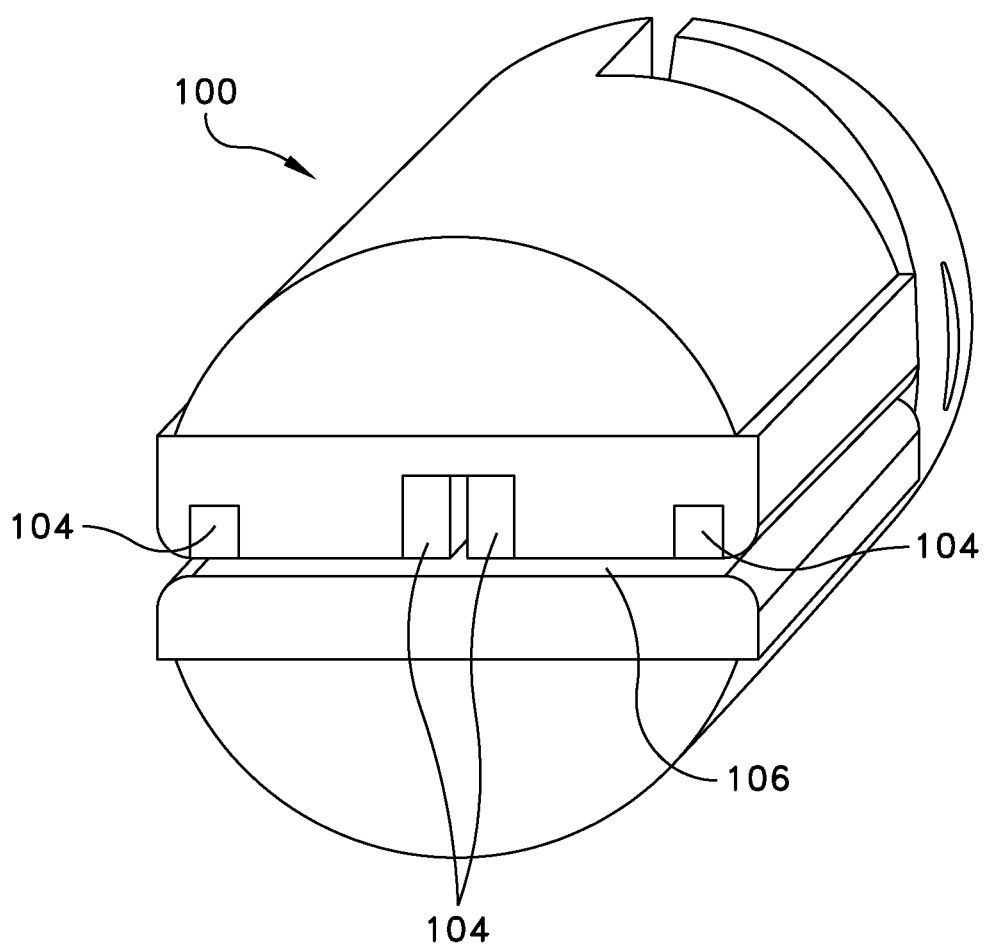
Figure 21:
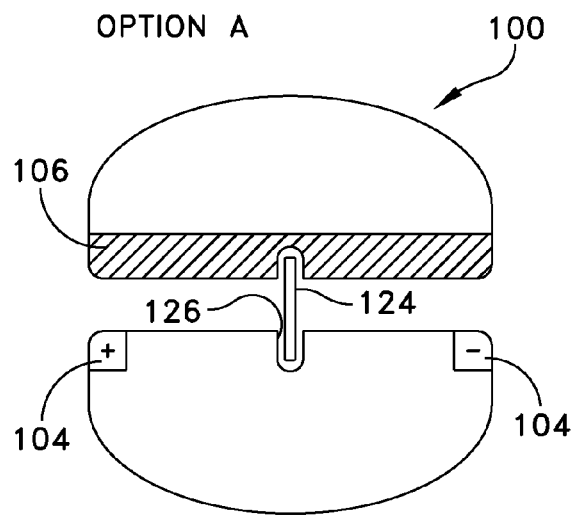
Figure 22:
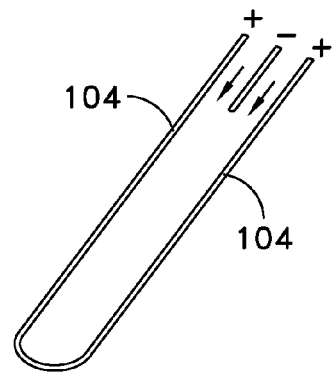
Figure 23:
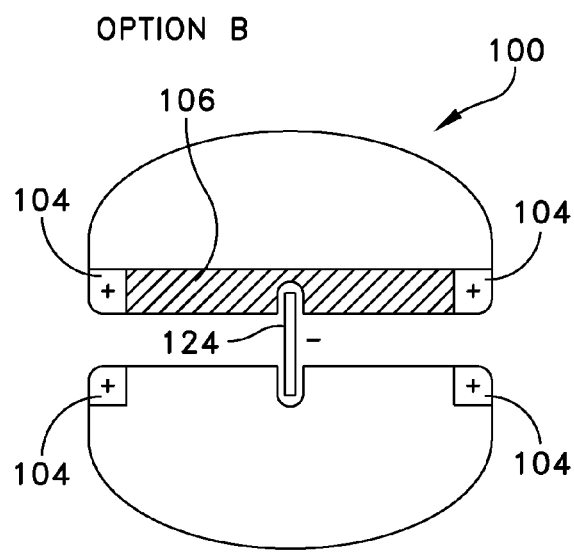
Figure 24:
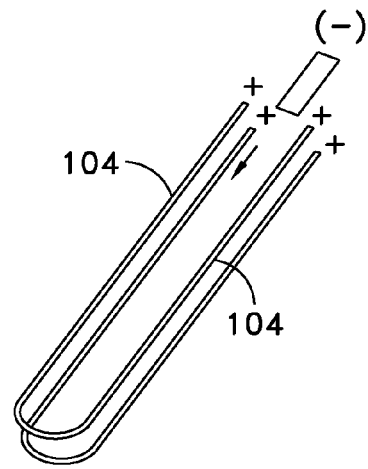
Figure 25:
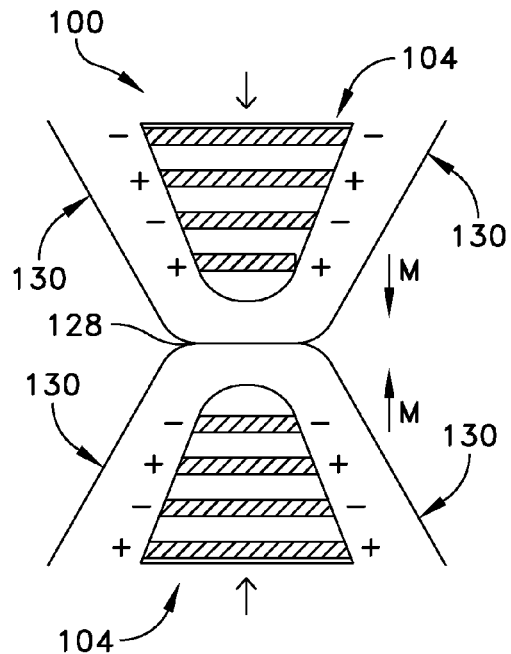
Figure 26:
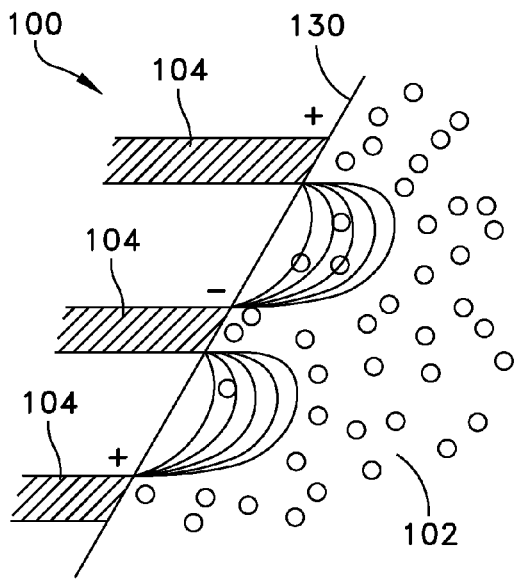
Figure 27:
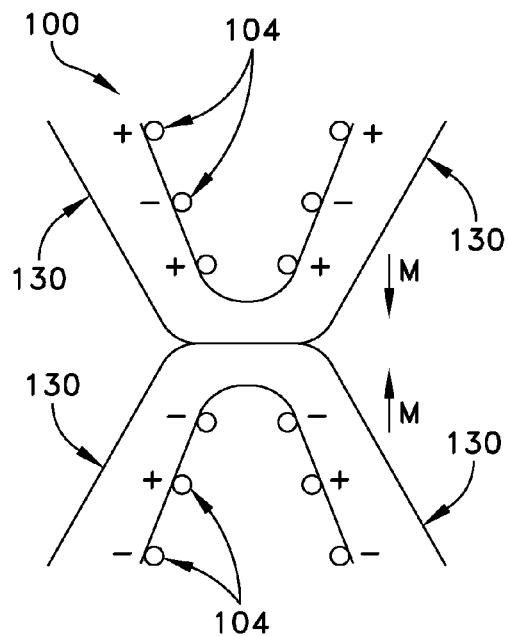
Figure 28:
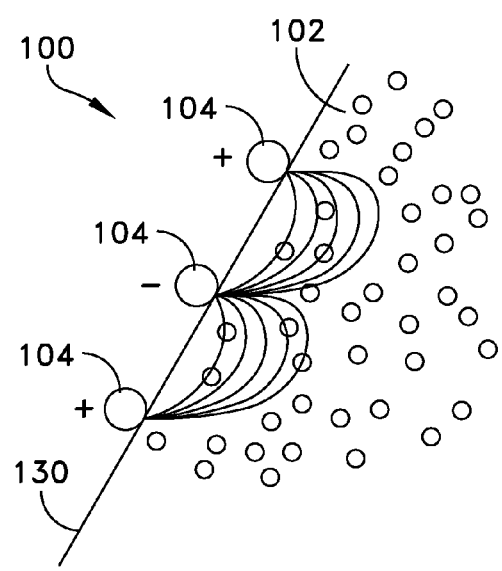

Referring still to FIGS. 12-15, there is shown a pressure controller 116 in operable connection with the set of jaws 114. Pressure controller 116 may include a low pressure setting at location 118 and a high pressure setting at location 120 (FIG. 15). Low pressure setting may be configured to allow jaws 114A, 114B to apply a low amount of pressure so as to grasp and approximate tissue without excessive damage to the tissue. High pressure setting may be configured to allow the jaws 114A, 114B to apply a high amount of pressure so as to clamp the tissue for welding with energy applicator 104 and biopolymer applicator 106. For example, pressure controller 116 may include, at the high pressure setting at location 118, an initial set-point during initial activation of energy applicator 104. At location 120, pressure controller may also provide an escalating pressure up to a maximum set-point subsequent to initial activation of energy applicator 104.

In one embodiment, biopolymer applicator 106 provides a delivery mechanism for passively delivering biopolymer 108 into thermally welded tissue to structurally reinforce the weld. There may be provided two opposing jaw members 114A, 114B, which are capable of approximating and clamping target tissue 102. Bipolar radio-frequency energy may be conducted through target tissue 102 to cause localized heating. Energy may be applied up to the point where the intracellular and extracellular water is evaporated from target tissue 102 and the collagen and elastin are denatured. This initial coagulation necrosis may be described as a loose entanglement of the denatured collagen and elastin fibers.

As heat is generated within tissue 102, it is thermally transferred into porous plate 106 located within inner face of jaw 114 or into another tissue-contacting region 102B, 102C. Porous plate 106 is embedded with biopolymer 108, such that biopolymer 108 is contained within the pores of plate 106. As porous plate 106 is heated, biopolymer 108 changes from a solid to a molten state and is drawn or wicked into target tissue 106 by capillary action. The molten low viscosity bioabsorbable polymer fills the voids between the denatured collagen and elastin thereby reinforcing the weld and providing a hermetic seal once polymer 108 has cooled.

As illustrated in exemplary embodiments shown in FIGS. 21-24, a knife 124 may be provided for division of target tissue 102. At least one of jaws 114A, 114B may form a knife channel 126 therein containing knife 124, wherein the knife extends from knife channel 126. In an embodiment, knife 124 is an electrode portion of a radio-frequency applicator of energy applicator 104.

Figure 32:
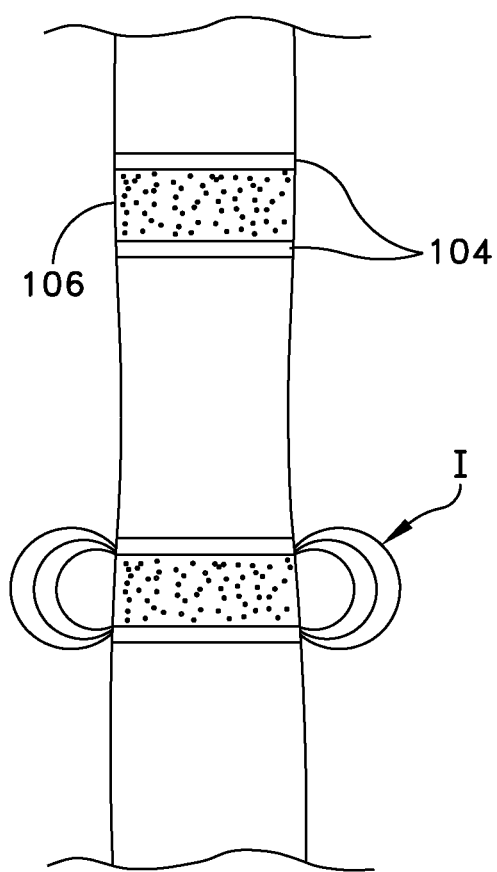

Apparatus 100 may be provided in various configurations for a variety of procedures. In an embodiment, energy applicator 104 and biopolymer applicator 106 may be configured for liver resection or solid organ resection. The parenchymal tissue is divided by blunt dissection or by a crush technique by mechanism of closing a hinged pair of jaws and physically dividing the tissue. Energy applicator and biopolymer applicator are configured on the sides of the jaws surface in order to deliver biopolymer to the exposed parenchymal tissue adjacent to the device and to create a hemostatic barrier. As illustrated in FIGS. 25-28, a hinged portion 128, energy applicator and biopolymer applicator may be provided on apparatus 100 to engage with tissue or parenchyma 130 for liver resection or solid organ resection. FIGS. 29-31 illustrate an embodiment of apparatus 100 with energy applicator 104 and biopolymer applicator 106. As illustrated in FIG. 32, energy applicator 104 and biopolymer applicator 106 may be configured to heat and to deliver biopolymer in an annular or ring-shaped fashion. This is particularly useful for procedures where creating structural rigidity of an annular or ring-shaped section of tissue is desired such as for improving sphincter control in patients with urinary incontinence or creating rigidity of the uvula in somnoplasty.

The inner electrode deploys distally. Attached to the distal end of the inner electrode may be a knife edge for dividing tissue. Energy can be delivered as the inner electrode is deployed distally or after the inner electrode is fully deployed. This electrical configuration is first described by Wappler, et al. in U.S. Pat. No. 2,031,682. Other patents that describe deployable knife/electrodes are U.S. Pat. No. 6,652,521 and U.S. Pat. No. 7,087,054.

In another embodiment, energy applicator 104 may be positioned adjacent a first tissue contacting surface 102A and may be configured to apply an amount of energy to generate heat within target tissue 102. The heat evaporates intracellular and extracellular water from target tissue 102 to create dried tissue. Biopolymer applicator 106 may be disposed at second tissue contacting surface 102B. Biopolymer applicator 106 may be configured for housing biopolymer material 108 at a location adjacent to target tissue 102. The heat generated allows biopolymer material 108 to change phase from a solid state to a molten state. Biopolymer material 108 fills the dried tissue so as to provide a hemostatic barrier once biopolymer material 108 cools and returns to the solid state. In applications for creating a hemostatic barrier, or to provide structural rigidity of surrounding native tissue, direct tissue compression is not required. An electrode or energy source may be simply placed in contact with the target tissue causing desiccation. The porous plate remains adjacent, and in contact with, target tissue 102 to deliver the molten biopolymer material 108.

Figure 33:
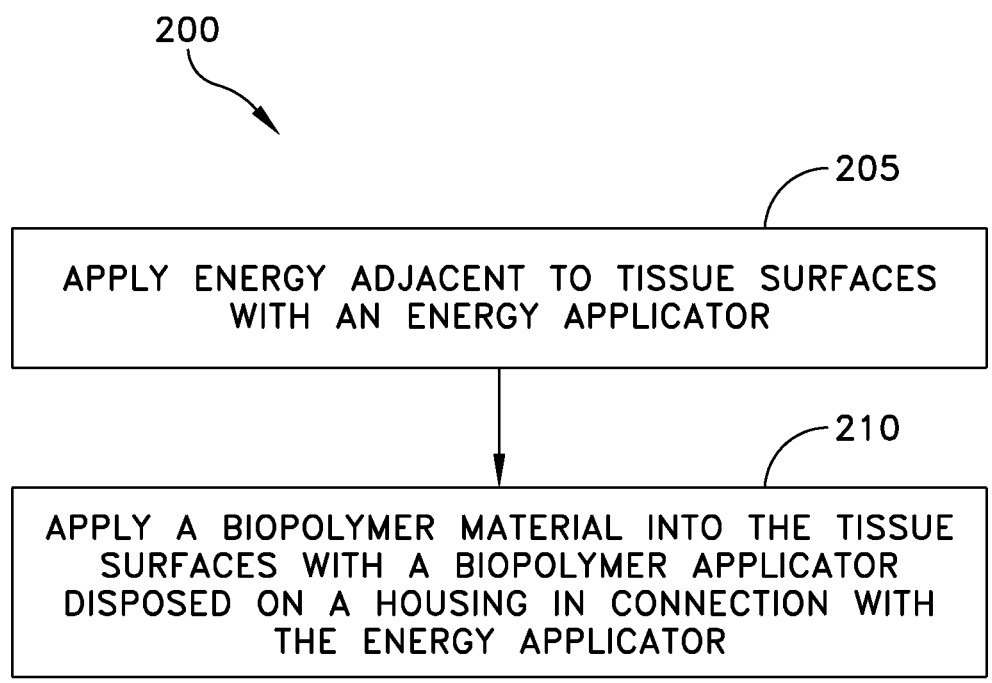
FIGS. 33 and 34 illustrate exemplary methods of applying energy and applying a biopolymer material into tissue.

Referring to FIG. 33, there is provided a method 200 of attaching and reinforcing tissue. Method 200 may include applying 205 energy adjacent to tissue surfaces with an energy applicator. Application of the energy may be configured to generate an amount of heat within the tissue surfaces. The heat evaporates intracellular and extracellular water from the target tissue to create dried tissue. The heat also denatures collagen and elastin within the tissue surfaces to attach portions of the tissue surfaces to one another. Method 200 may further include applying 210 a biopolymer material into the tissue surfaces with a biopolymer applicator disposed on a housing in connection with the energy applicator. Application of the biopolymer material may include housing the biopolymer material at a location adjacent to the tissue surfaces to receive the heat generated by the energy applied to the target tissue. This heat allows the biopolymer material to change phase from a solid state to a molten state. The heat also allows the biopolymer to fill the dried tissue so as to reinforce the attach portions of the tissue portions and provide a hermetic seal once the biopolymer cools and returns to the solid state.

Figure 34:
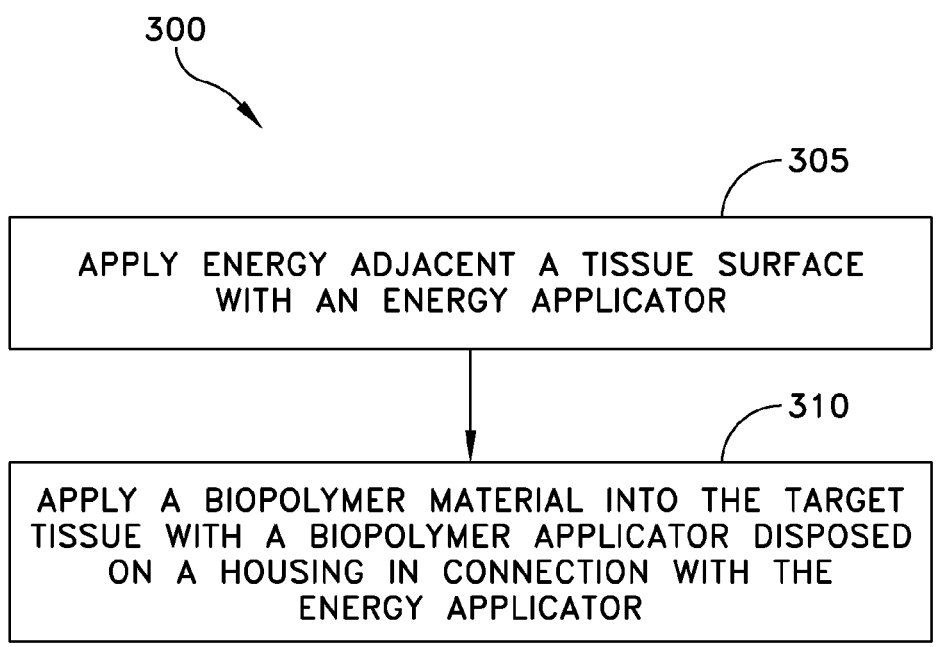

Referring to FIG. 34, there is provided a method 300 of reinforcing tissue. Method 300 may include applying 305 energy adjacent a tissue surface with an energy applicator. Application of the energy may be configured to generate an amount of heat within a target tissue. The heat evaporates intracellular and extracellular water from the target tissue to create dried tissue. Method 300 may further include applying 310 a biopolymer material into the target tissue with a biopolymer applicator disposed on a housing in connection with the energy applicator. Application of the biopolymer includes housing the biopolymer material at a location adjacent to the target tissue to receive the heat generated by the energy applied to the target tissue. The heat allows the biopolymer material to change phase from a solid state to a molten state. The biopolymer fills the dried tissue so as to provide a hemostatic barrier once the biopolymer cools and returns to the solid state.

Tissue Welder

In various embodiments, there may be provided a RF tissue welder for use in joining, attaching, resecting, bulking and/or ligating tissue structures (such as, but not limited to: lung, bowel, gastric, arteries, veins, bladder, fascia, peritoneum, muscle).

This tissue welder may provide a more optimal RF energy delivery for a grasping hemostat style surgical device (open or endoscopic) that incorporates an offset electrode design. RF energy is transmitted as high frequency alternating current passed through electrodes, which cause ionic agitation, or friction of the target tissue resulting in localized heating. During application of RF energy, the target tissue is simultaneously compressed and heated, resulting in the evaporation of water and the fusing of the native collagen and elastin by denaturing and physical entanglement of protein chains. The process of heating with RF results in a rate limited denaturization of collagen at approximately 60 degrees Celsius and is highly dependent on time and temperature. When temperatures reach approximately 100 degrees Celsius, desiccation of the tissue occurs as intracellular and extracellular water is evaporated off. Elastin denaturation occurs at significantly higher temperatures (above 130 degrees Celsius).

Current prior art is generally described either as electrodes which are diametrically opposed, electrodes which are offset, or as electrodes comprising a deployable inner electrode (as described by Wappler et. all; U.S. Pat. No. 2,068,721). In both the latter designs, electrical current travels parallel to the compressed tissue planes as opposed to in a direction normal to the tissue plane.

Embodiments of the RF tissue welder described herein provide a more optimal energy delivery for the case where current flows parallel to the target tissue plane. It has been shown that a focused line of desiccation develops nearly equidistant between the electrodes. This line of desiccation is visibly identified and is characterized as a localized area of high electrical impedance. Two issues result from the development of this localized area of desiccation. The ability to evenly heat and uniformly weld the target tissue is diminished as impedance rises at the line of desiccation. This developed line of desiccation acts as an insulative barrier. Continued heating can be achieved by raising the RF voltage; however, the majority of work (as measured in Joules) completed in the form of heating is achieved at the line of desiccation causing a localized hot spot potentially resulting in tissue vaporization and tissue cutting. Methods are provided herein to minimize the line of desiccation and to evenly distribute heating across the target tissue.

Considerable work has been completed in the areas of energy-based tissue welding using laser, ultrasonic, radio-frequency (RF) energy, or direct thermal cautery. RF tissue welding technologies are commercially available to seal and ligate small blood vessels (Covidien—LigaSure™, SurgRx™—J&J/Ethicon, Gyrus PLC—Olympus, etc.). With current vessel sealing technology, RF energy is directed into the target tissue which is locally heated. Electrical current, voltage and power are adjusted using a closed-loop control algorithm based on feedback variables (impedance, time, temperature, phase, current, power, voltage, etc.). The mechanism of fusing tissue in opposite layers relies on collagen and elastin protein denaturation in combination with tissue compression to create a physical entanglement of protein chains. The effected tissue is thermally damaged and non-viable. The acute inflammatory response to the thermal injury is minimal, and the proliferative phase (fibroblast and collagen deposition) of wound healing is believed to last between 2 to 4 weeks, although strength can be comparative to native tissue in as little as 7 days. A significant advantage of RF-energy tissue sealers is the ability to reduce the overall device size as compared to larger mechanical suture devices (due to design flexibility with wiring and electrodes) further enabling minimally invasive surgery. As identified above, it has been shown that a focused line of desiccation develops nearly equidistant between the electrodes. This line of desiccation is easily visibly identified and is a localized area of high tissue impedance. Tissue impedance rises considerably with the application of heat as irreversible damage occurs to the target tissue. For temperatures from 40° C. up to 100° C. this is a first order rate limited degradation commonly described by the Arrhenius Equation:

$$k = Ae^{-E_a/RT}$$

The relationship between temperature and tissue impedance is further complicated as phase changes in the non-homogenous tissue structure occurs such as when the tissue approaches 100° C. and intracellular and extracellular water is driven off. However, it is always observed that tissue impedance increases with time and temperature. The development of a localized line of desiccation is related to an initial thermal imbalance as the tissue heats. This imbalance is created as the electrodes themselves and surrounding materials act as heat sink, causing the tissue adjacent to the electrode to be cooler than the tissue located equidistant or between the electrodes. The change in tissue temperature can be described by the bioheat equation, where the effects of perfusion and metabolic processes are considered to be negligible. The bio-heat equation:

$$\rho c \frac{\partial T}{\partial t} = \nabla(k\nabla T) + q_s + q_p + q_m$$

As tissue impeaance rises witn an increase in temperature, the impedance of the tissue located equidistant or between the electrodes also rises. The majority of work (Joules) is completed at the area of high impedance. This creates a positive feedback loop, causing the area equidistant to or between the electrodes to sharply rise in temperature. The tissue can be described in a simple model as a two-dimensional chain of temperature dependent variable resistors in series. If heat is higher at the center of the chain, impedance will rise faster in center. The higher impedance will cause increased heating to occur at the center, causing a positive feedback loop. This results in a highly defined and narrow line of desiccation between the electrodes.

The effects of this line of desiccation can be controlled and minimized with two approaches. One is to select electrode and end-effector materials with high coefficients of thermal conductivity so as to evenly distribute heat within the targeted tissue area. Materials selected should be electrically insulative and have coefficients of thermal conductivity greater than approximately 10 W/mK and have electrical resistivity in the range of $10^{12}$ to $10^{16}$ ohm-cm. Materials should also be capable of resisting surface breakdown and tracking as measured by a Comparative Tracking Index (ASTM D3638) greater than 300V. Additionally, materials in contact with the target tissue should have a low thermal mass or be thermally insulated from the rest of the end-effector, so as not to divert energy required for tissue fusion back into the device. Examples of such materials include, but are not limited to: Polyimide (PI), Polyamide-imine (PAI), Polyphthalamide (PPA), Polyphenylene Sulfide (PPS), Liquid Crystalline Polymer (LCP), and Silicone where materials have been formulated with an thermally conductive filler (such as, but not limited to Boron Nitride). The second approach to minimizing the line of desiccation is to regulate voltage such that voltage does not exceed a maximum value determined by electrode offset distance. High voltage at the end of the energy delivery cycle (after the initial impedance rise) has been shown to cause tissue vaporization and tissue cutting. The upper threshold for acceptable voltage has been shown to be approximately 100 V(rms)/mm in relationship to the minimum electrode offset spacing for electrodes less than 10 mm apart.

Figure 35:
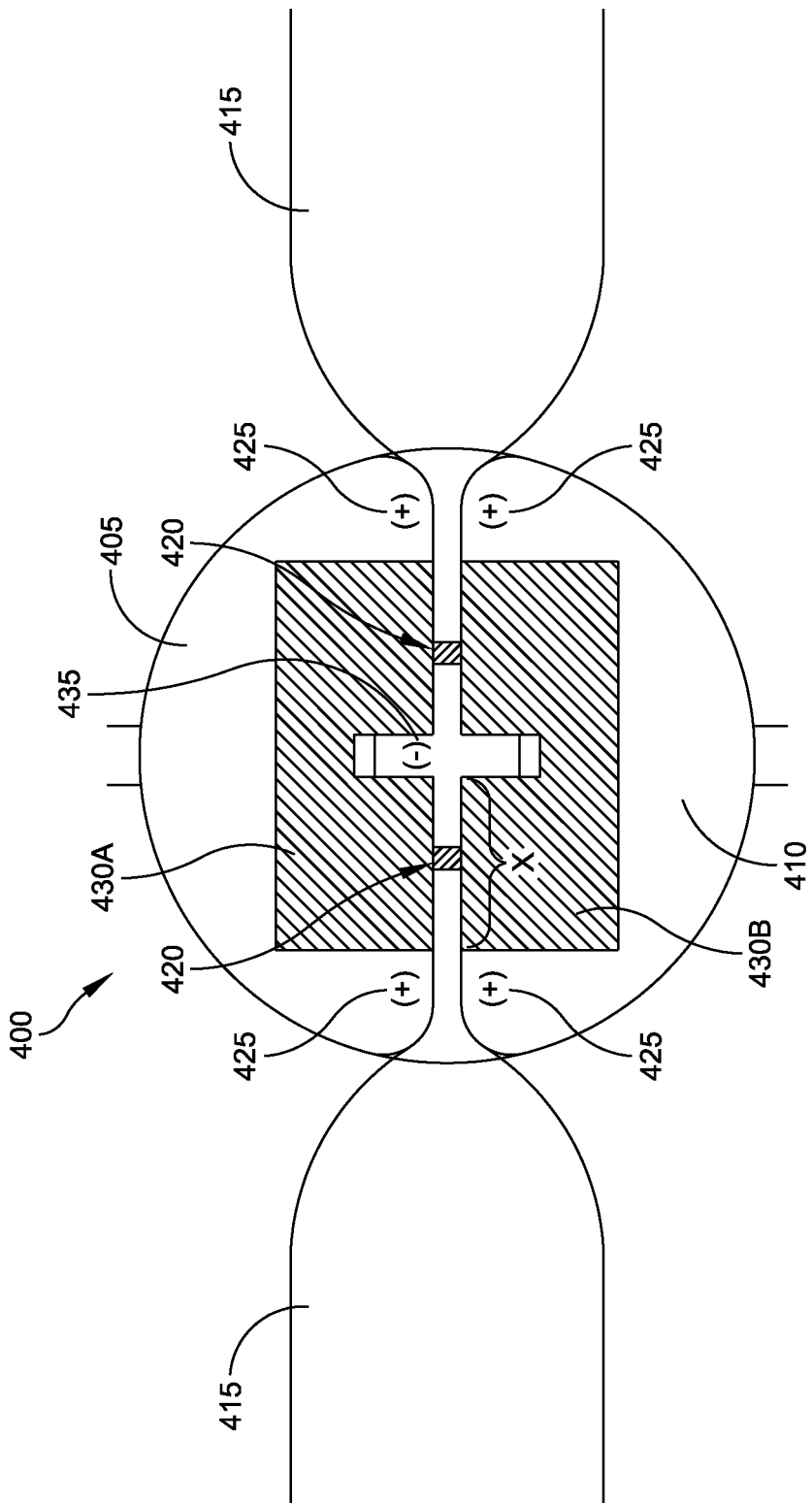
FIGS. 35-41 illustrate exemplary embodiments of jaw effectors for attachment and reinforcement of tissue with radio frequency energy sources.
Figure 36:
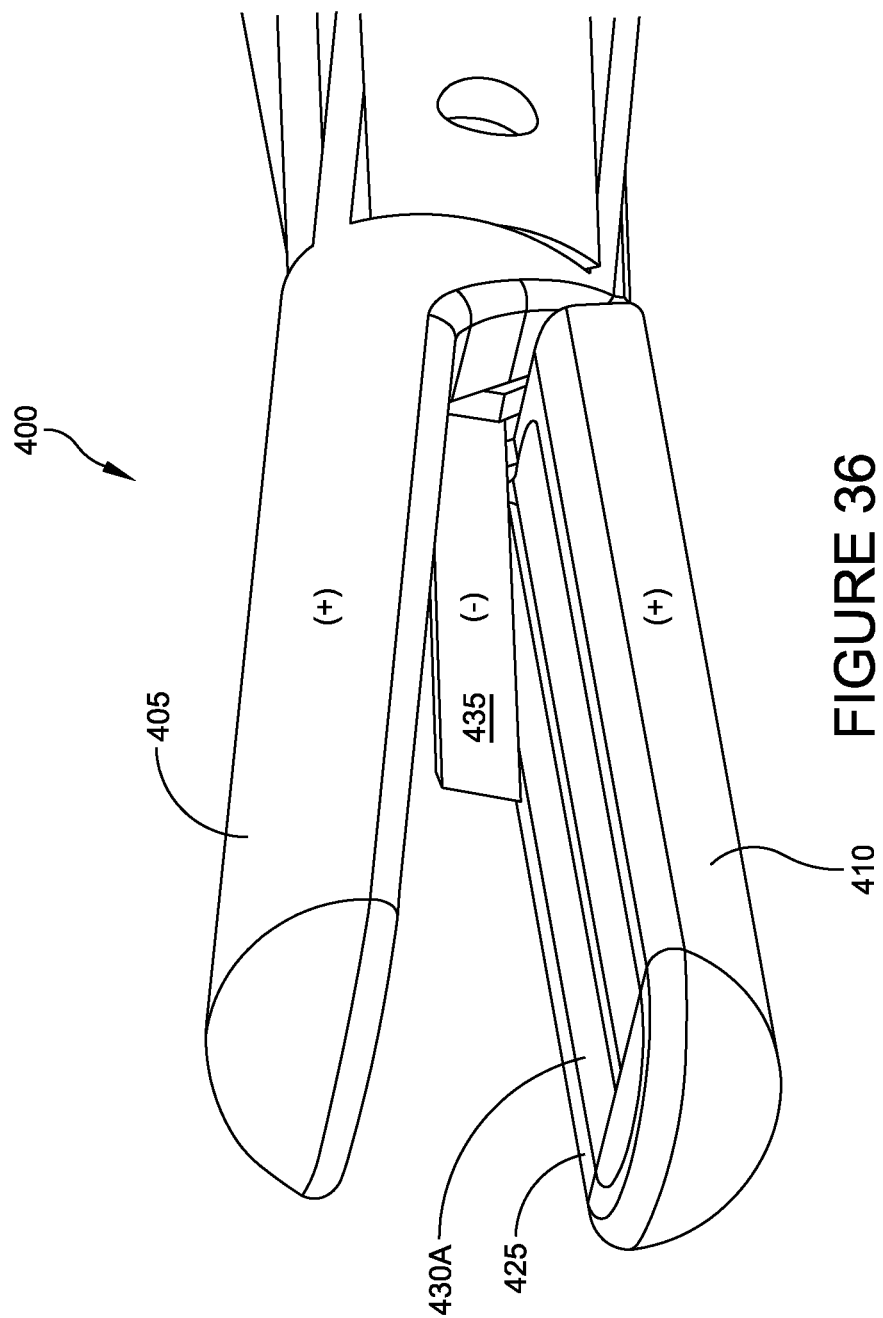

Referring to FIGS. 35 and 36, and in an embodiment, there is provided a tissue welder device 400 having two opposing jaw members 405, 410, which may be characterized, but are not limited to, as upper jaw member 405 and lower jaw member 410. In an embodiment, jaw members 405, 410 are capable of approximating and clamping target tissue 415 with in the pressure range of about 5 to about 10 kgf/cm². Bipolar radio-frequency energy 420 is conducted through the target tissue 415 to flow in a direction parallel to the application of compression force to the general compressed tissue plane so as to cause localized heating. In an embodiment, two opposing jaws 405, 410 are aligned to mate with one another at the same at the same electrical potential (shown as positive, for example) and contact tissue 415 directly along electrodes at edge portions 425 (or perimeter 425) of the clamped target tissue zone. The jaw design may incorporate a non-conductive insert 430A, 430B placed within jaws 405, 410, capable of transferring applied pressure to the clamped target tissue. An inner electrode 435 at a second potential (shown as negative, for example) is deployed between the opposing jaws 405, 410 and is insulated by the non-conductive inserts 430A, 430B, such that electrical current 420 flows through the target tissue 415. In an embodiment, applied voltage does not exceed about 100 V(rms)/mm measured as the minimum distance from the inner electrode 435 to either side of the opposing jaws serving as an outer electrode 425.

Offset is as an electrode configuration in which electrodes located one jaw are not geometrically or directly opposed to an electrode of a different potential or polarity located on the corresponding mating jaw. This offset is shown schematically in FIGS. 37-41 with the offset width denoted as an "x".

Figure 37:
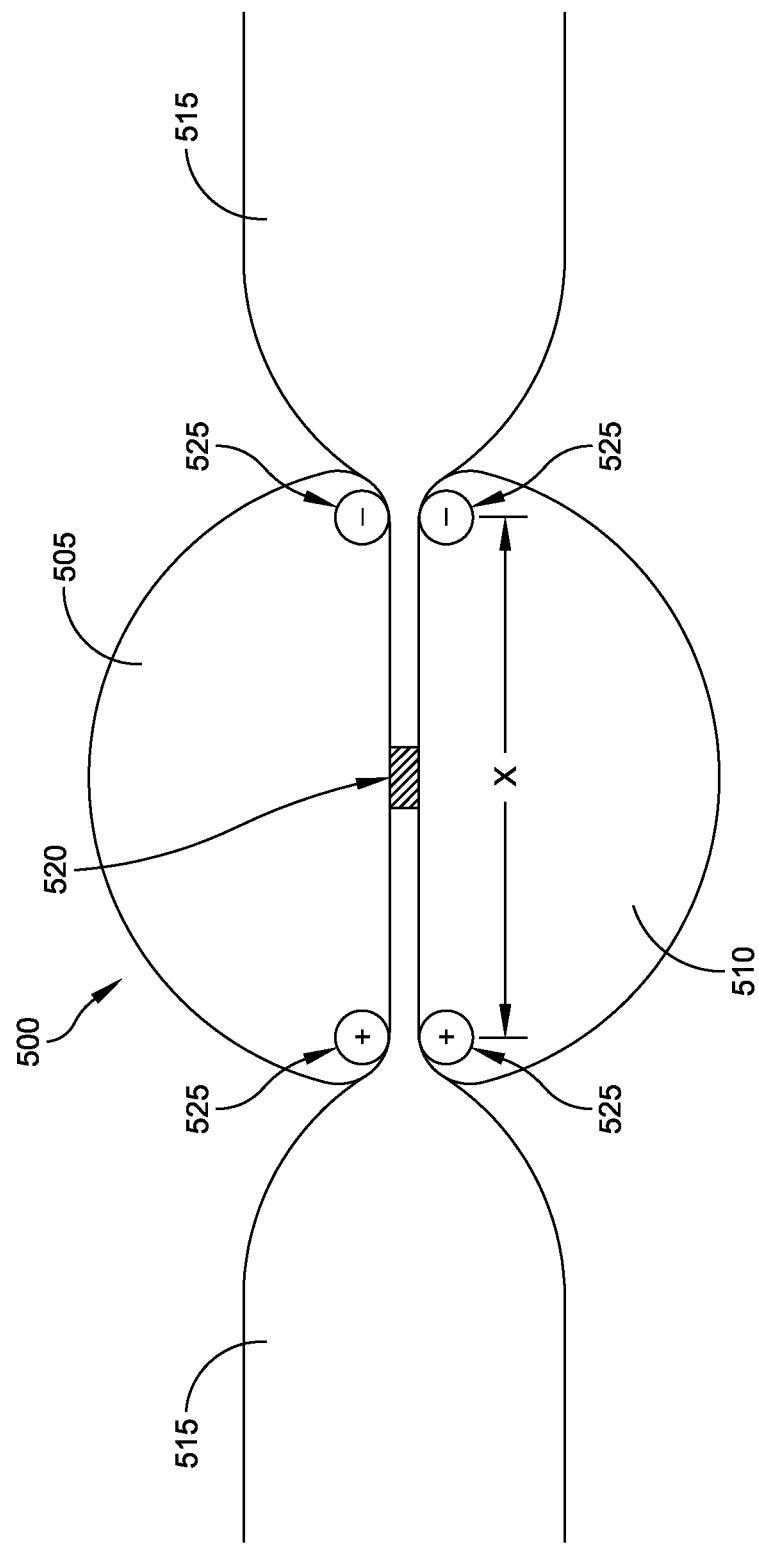

Referring now to FIG. 37, there may be provided a tissue welder device 500 having two opposing jaw members 505, 510, which may be characterized, but are not limited to, as upper jaw member 505 and lower jaw member 510. In an embodiment, jaw members 505, 510 are capable of approximating and clamping target tissue 515 with in the pressure range of about 5 to about 10 kgf/cm$^2$. Bipolar radio-frequency energy 520 is conducted through the target tissue 515 to flow in a direction parallel to the application of compression force to the general compressed tissue plane so as to cause localized heating. The electrodes 525 are configured such that current flows in a side-to-side (parallel) manner across the width or length of the jaws 505, 510. This can be achieved using electrodes offset from each other along the width or length of the grasping jaw, either on the same tissue-contacting surface or on opposing tissue contacting surfaces.

Figure 38:
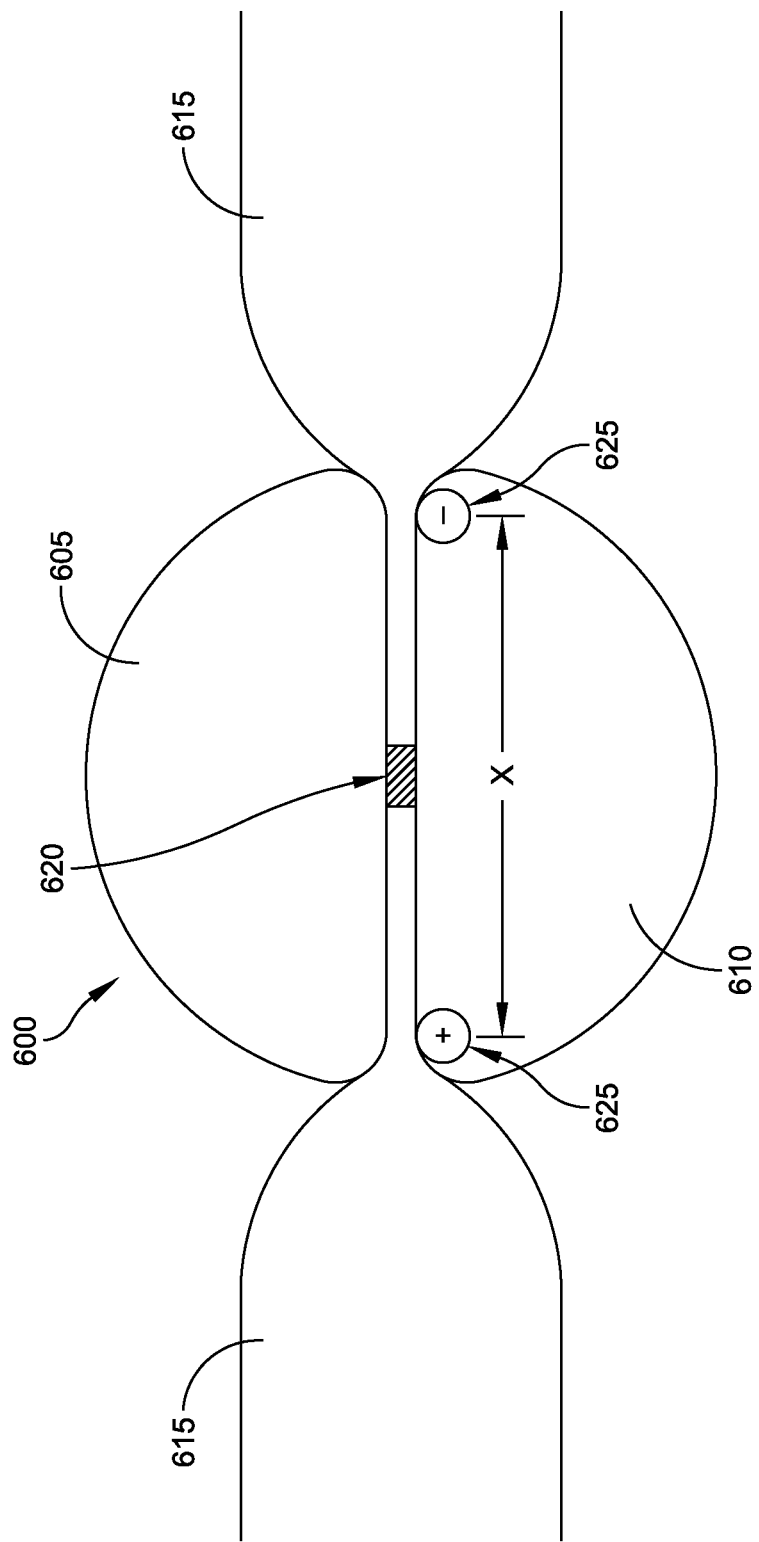

With reference to FIG. 38, there may be provided a tissue welder device 600 having an offset configuration with electrodes 625 located on only one jaw surface. Electrodes 625 of differing electrical potentials are spaced apart with current flowing substantially planar to the clamped tissue. Two opposing jaw members 605, 610, which may be characterized, but are not limited to, as upper jaw member 605 and lower jaw member 610. In an embodiment, jaw members 605, 610 are capable of approximating and clamping target tissue 615 with in the pressure range of about 5 to about 10 kgf/cm$^2$. Bipolar radio-frequency energy 620 is conducted through the target tissue 615 to flow in a direction parallel to the application of compression force to the general compressed tissue plane so as to cause localized heating. The electrodes 625 are configured such that current flows in a side-to-side (parallel) manner across the width of jaws 610. This can be achieved using electrodes offset from each other along the width or length of the grasping jaw, either on the same tissue-contacting surface or on opposing tissue contacting surfaces.

Figure 39:
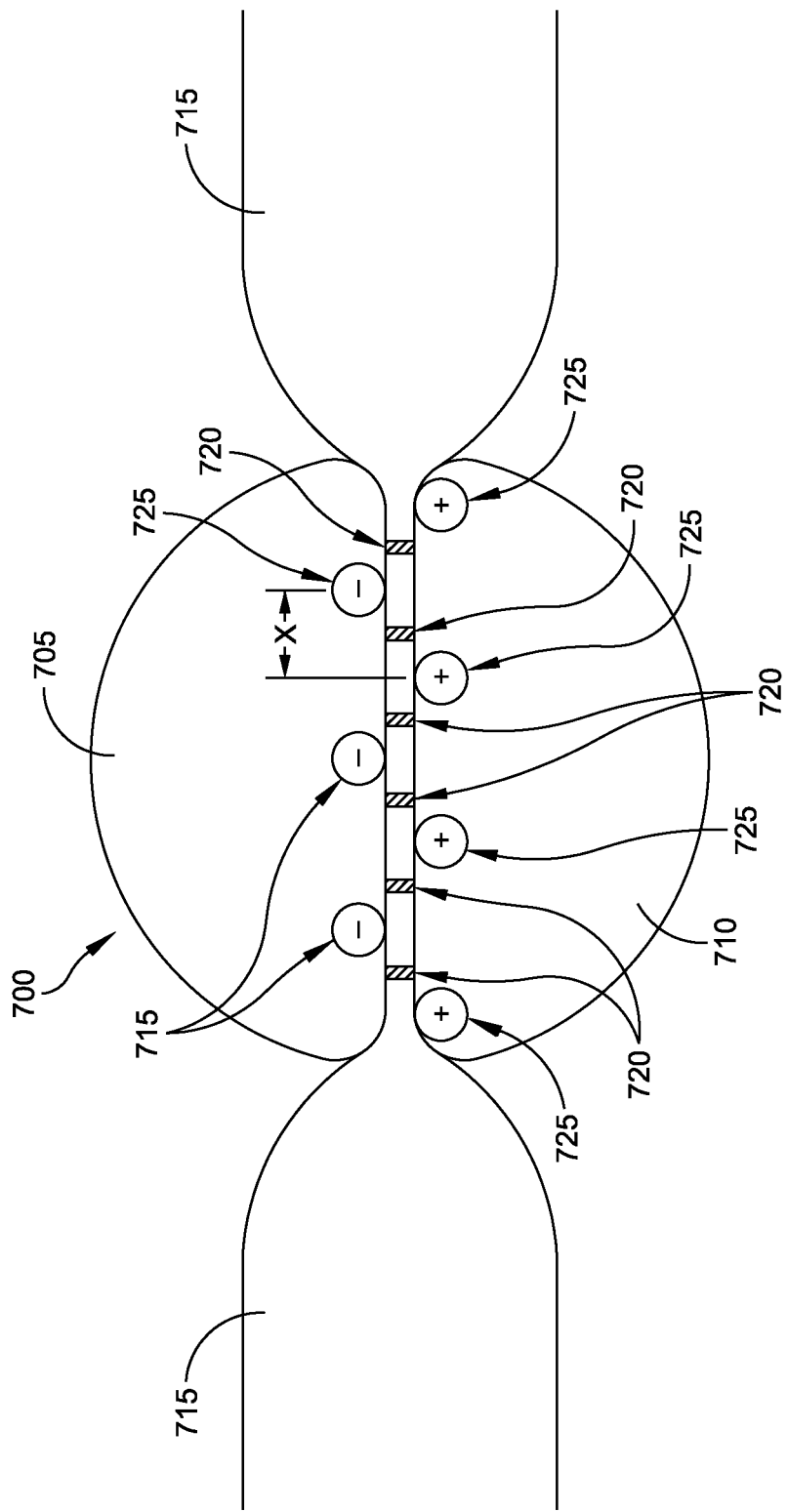

With reference to FIG. 39, offset configurations can include a plurality of electrode sets. In an embodiment, there may be provided a tissue welder device 700 having two opposing jaw members 705, 710, which may be characterized, but are not limited to, as upper jaw member 705 and lower jaw member 710. In an embodiment, jaw members 705, 710 are capable of approximating and clamping target tissue 715 with in the pressure range of about 5 to about 10 kgf/cm$^2$. Bipolar radio-frequency energy 720 is conducted through the target tissue 715 to flow at multiple discrete locations in a direction substantially parallel to the application of compression force to the general compressed tissue plane so as to cause localized heating. The plurality of electrodes 725 are configured such that current flows in a side-to-side (parallel) manner across the width or length of the jaws 705, 710. This can be achieved using electrodes 725 offset from each other along the width or length of the grasping jaw 705, 710, either on the same tissue-contacting surface or on opposing tissue contacting surfaces. In one embodiment, voltage does not exceed about 100 V(rms)/mm measured as the minimum distance between offset electrodes.

Figure 40:
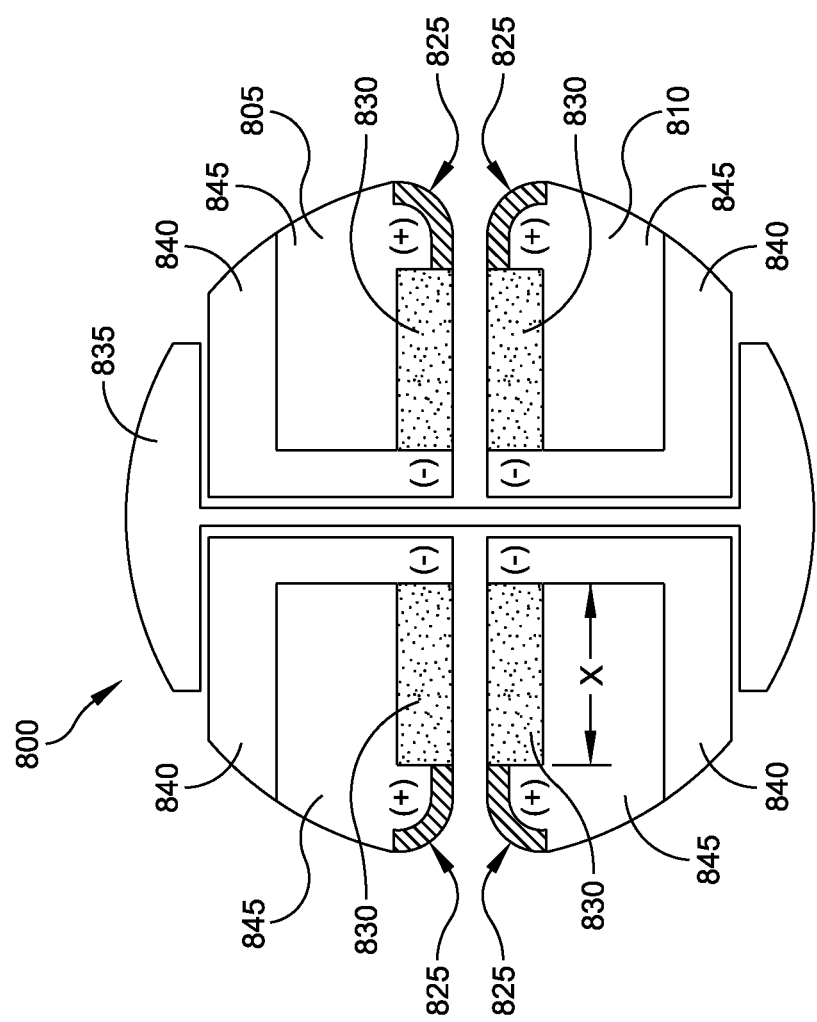
Figure 41:
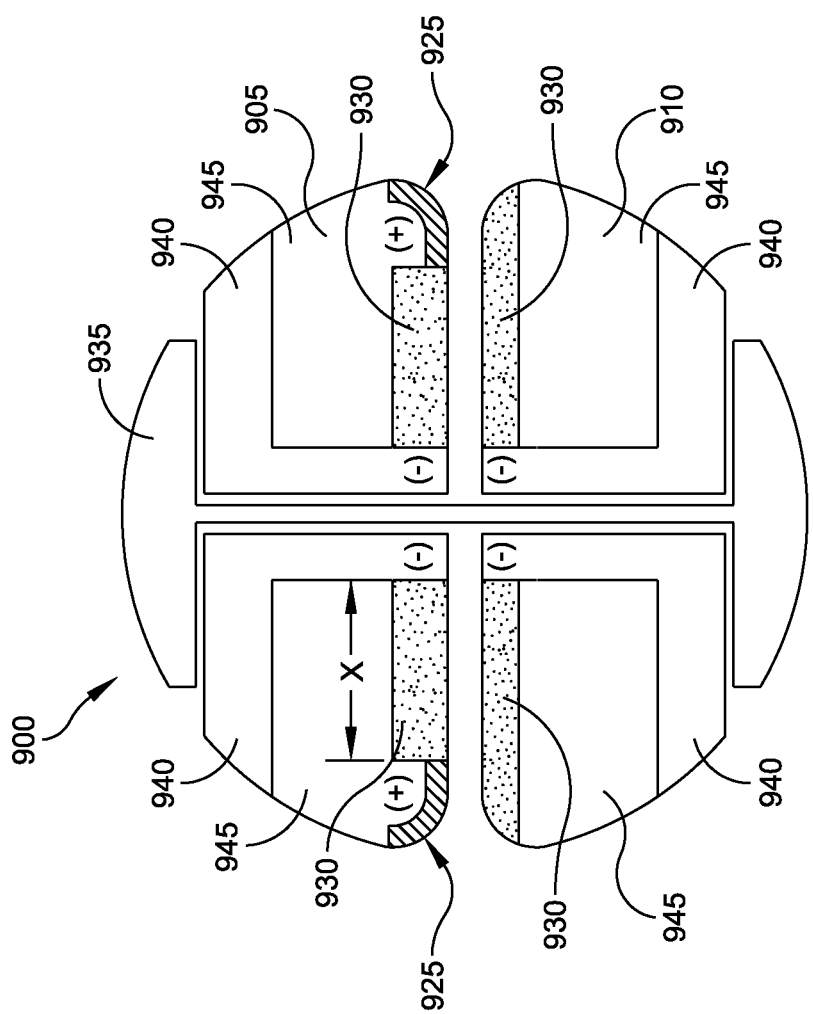

Referring to FIGS. 40 and 41, and in exemplary embodiments, inner electrode 840/940 may incorporate a knife 835/935 capable of separating the target tissue (not shown.)

Referring to FIG. 40, electrical potential can be applied to inner electrodes 840 independent of knife member 835, or electrical potential can be applied directly to knife member 840. A tissue welder device 800 may have two opposing jaw members 805, 810, which may be characterized, but are not limited to, as upper jaw member 805 and lower jaw member 810. In an embodiment, jaw members 805, 810 are capable of approximating and clamping target tissue 815 with in the pressure range of about 5 to about 10 kgf/cm$^2$. Bipolar radio-frequency energy is conducted through the target tissue to flow in a direction parallel to the application of compression force to the general compressed tissue plane so as to cause localized heating. The electrodes 825 are configured such that current flows in a side-to-side (parallel) manner across the width or length of the jaws 805, 810. Thermally conductive material 830 is provided to dissipate heat traveling across the tissue contact face of jaws 805, 810. Conventional thermoplastic 845 may form other portions of the jaws 805, 810 away from thermally conductive material 830 of tissue contact face of jaws 805, 810.

Referring to FIG. 41, electrical potential can be applied to inner electrodes 940 independent of knife member 935, or electrical potential can be applied directly to knife member 940. A tissue welder device 900 may have two opposing jaw members 905, 910, which may be characterized, but are not limited to, as upper jaw member 905 and lower jaw member 910. In an embodiment, jaw members 905, 910 are capable of approximating and clamping target tissue 915 with in the pressure range of about 5 to about 10 kgf/cm$^2$. Bipolar radio-frequency energy is conducted through the target tissue to flow in a direction parallel to the application of compression force to the general compressed tissue plane so as to cause localized heating. The electrodes 925 are configured on jaw 905 such that current flows in a side-to-side (parallel) manner across the width or length of the jaws 905, 910. Thermally conductive material 930 is provided to dissipate heat traveling across the tissue contact face of jaws 905, 910. Conventional thermoplastic 945 may form other portions of the jaws 905, 910 away from thermally conductive material 930 of tissue contact face of jaws 905, 910.

Figure 42:
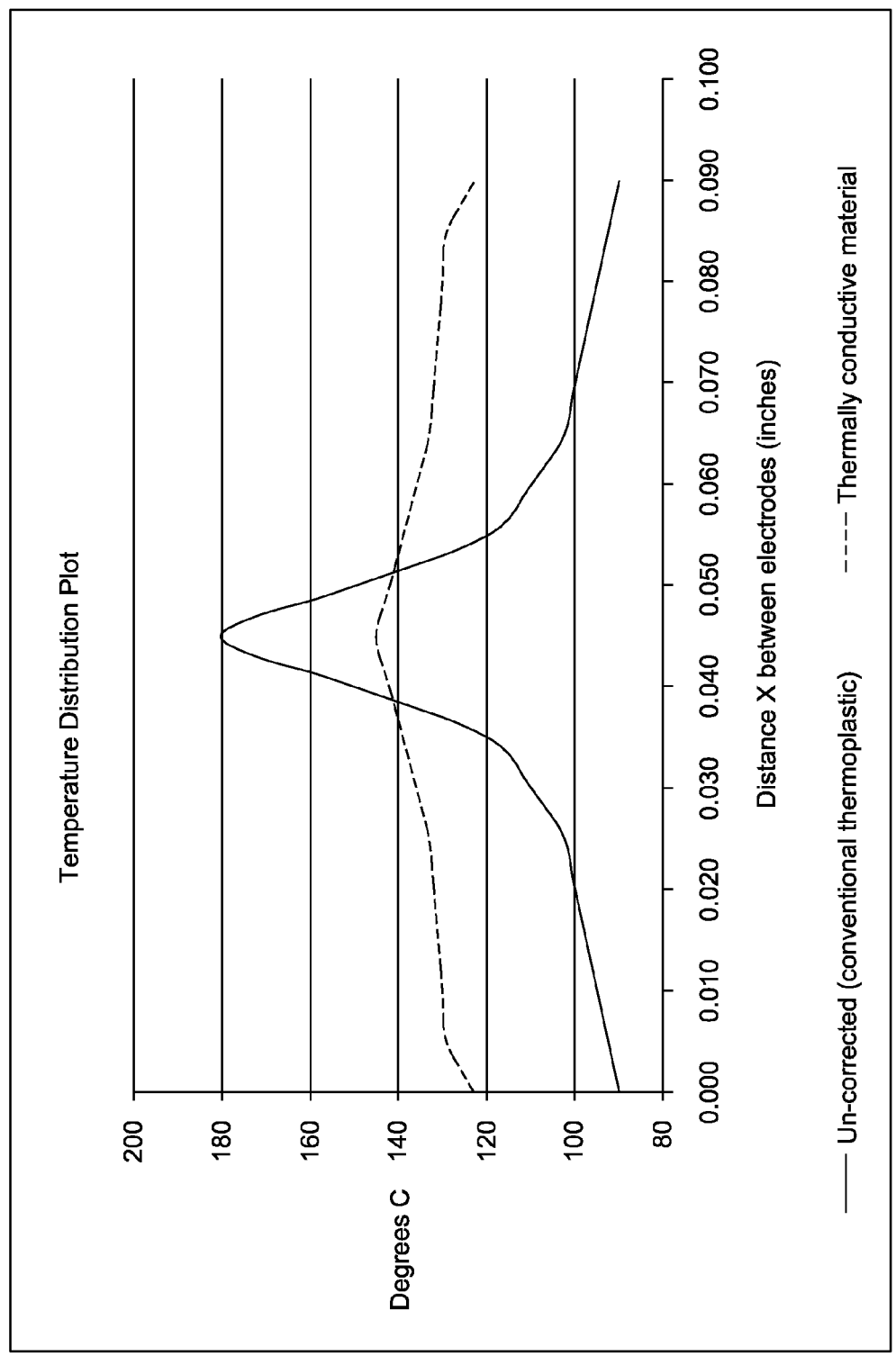
FIG. 42 illustrates a temperature distribution plot for the measured tissue temperature of an embodiment incorporating thermally conductive material in comparison to an un-corrected conventional thermoplastic.

Referring to FIG. 42, there is shown a temperature distribution plot for the measured tissue temperature of an embodiment incorporating a thermally conductive material in comparison to an un-corrected conventional thermoplastic with various identified distances between electrodes.

While the present invention has been described with reference to one or more preferred embodiments, which embodiments have been set forth in considerable detail for the purposes of making a complete disclosure of the invention, such embodiments are merely exemplary and are not intended to be limiting or represent an exhaustive enumeration of all aspects of the invention. Further, it will be apparent to those of skill in the art that numerous changes may be made in such details without departing from the spirit and the principles of the invention.

What is claimed is:

1. Apparatus for attachment and welding of tissue, the apparatus comprising:

an energy applicator positioned adjacent a first tissue contacting surface, the energy applicator configured to apply an amount of energy to generate heat within a target tissue so as to evaporate intracellular and extracellular water from the target tissue to create dried tissue, and denature at least one of collagen and elastin within the target tissue to attach portions of the target tissue together; and a thermally conductive material disposed at a second tissue contacting surface, the thermally conductive material configured for direct contact with the target tissue heated by the energy applicator, and the thermally conductive material providing a path of thermal conduction.

2. Apparatus in accordance with claim 1, wherein the thermally conductive material is a thermally conductive polymer.

3. Apparatus in accordance with claim 1, wherein the thermally conductive material is a biopolymer applicator.

4. Apparatus in accordance with claim 1, wherein the thermally conductive material is a porous plate.

5. Apparatus in accordance with claim 1, wherein the at least one of the first tissue contacting surface and the second tissue contacting surface include electrode materials and end-effector materials, and wherein the electrode materials and end-effector materials have a high coefficient of thermal conductivity so as to evenly distribute heat within the targeted tissue area.

6. Apparatus in accordance with claim 5, wherein at least one of the electrode materials and end-effector materials are electrically insulative.

7. Apparatus in accordance with claim 5, wherein at least one of the electrode materials and end-effector materials have coefficients of thermal conductivity greater than approximately 10 W/mK.

8. Apparatus in accordance with claim 5, wherein at least one of the electrode materials and end-effector materials have electrical resistivity in the range of $10^{12}$ to $10^{16}$ ohm-cm.

9. Apparatus in accordance with claim 5, wherein at least one of the electrode materials and end-effector materials resist surface breakdown and tracking as measured by a Comparative Tracking Index (ASTM D3638) at voltages greater than 300V.

10. Apparatus in accordance with claim 5, wherein at least one of the electrode materials and end-effector materials in contact with the target tissue have a low thermal mass and specific heat capacity less than approximately 1.30 J/g° C., so as not to divert energy required for tissue fusion back into the energy applicator.

11. Apparatus in accordance with claim 5, wherein at least one of the electrode materials and end-effector materials in contact with the target tissue are thermally insulated from other portions of the energy applicator so as not to divert energy required for tissue fusion back into the energy applicator.

12. Apparatus in accordance with claim 5, wherein at least one of the electrode materials and end-effector materials comprise a thermally conductive material including at least one of polyimide (PI), polyamide-imine (PAI), polyphthalamide (PPA), polyphenylene sulfide (PPS), liquid crystalline polymer (LCP), and silicone.

13. Apparatus in accordance with claim 12, wherein the thermally conductive material has been formulated with a thermally conductive filler.

14. Apparatus in accordance with claim 12, wherein the thermally conductive material comprises boron nitride.

15. Apparatus in accordance with claim 5, wherein the energy applicator includes a set of jaws.

16. Apparatus in accordance with claim 5, further comprising a pressure controller in operable connection with the set of jaws, wherein the pressure controller has a low pressure setting and a high pressure setting, wherein the low pressure setting is configured to allow the jaws to apply a low amount of pressure so as to grasp and approximate tissue without excessive damage to the tissue, and wherein the high pressure setting is configured to allow the jaws to apply a high amount of pressure so as to clamp the tissue for welding with the energy applicator and the thermally conductive material disposed at the at least one of the first tissue contacting surface and the second tissue contacting surface.

17. Apparatus in accordance with claim 5, further comprising a pressure controller in operable connection with a set of jaws, wherein the pressure controller is configured to allow the jaws to apply a pressure is between 5 to 10 kgf/cm2 and the pressure is distributed over substantially an entire portion of the tissue contacting surface.

18. Apparatus for attachment and welding of tissue, the apparatus comprising:

an energy applicator positioned adjacent at least one of a first tissue contacting surface and a second tissue contacting surface, the energy applicator configured to apply an amount of energy to generate heat within a target tissue so as to evaporate intracellular and extracellular water from the target tissue to create dried tissue, and denature at least one of collagen and elastin within the target tissue to attach portions of the target tissue together; and a thermally conductive material disposed adjacent the at least one of the first tissue contacting surface and the second tissue contacting surface, the thermally conductive material configured for direct contact with the target tissue heated by the energy applicator, and the thermally conductive material providing a high coefficient of thermal conductivity so as to evenly distribute heat within the targeted tissue area.

19. Apparatus in accordance with claim 18, wherein the energy applicator comprises electrodes offset by a distance, the electrodes configured to direct current flow through the compressed tissue in an direction coplanar to the at least one of the first tissue contacting surface and the second tissue contacting surface, and wherein the applied voltage does not exceed about 100 V(rms)/mm with respect to the offset electrode spacing between the electrodes.

20. Apparatus in accordance with claim 18, wherein the at least one of the first tissue contacting surface and the second tissue contacting surface comprises of a non-stick material.

21. Apparatus in accordance with claim 18, wherein the energy applicator comprises a knife for division of the target tissue.

22. Apparatus in accordance with claim 21, wherein the knife is attached to a deployable electrode portion of a radio-frequency applicator of the energy applicator.

23. Apparatus in accordance with claim 21, wherein the knife is configured to separate the target tissue during or after RF activation.

24. Apparatus in accordance with claim 18, wherein the non-stick material is PTFE.

25. Apparatus for attachment and welding of tissue, the apparatus comprising:

an energy applicator positioned adjacent at least one of a first tissue contacting surface and a second tissue contacting surface, the energy applicator configured to apply an amount of energy to generate heat within a target tissue so as to evaporate intracellular and extracellular water from the target tissue to create dried tissue, and denature at least one of collagen and elastin within the target tissue to attach portions of the target tissue together; and electrodes of the energy applicator offset by a distance, the electrodes configured to direct current flow through the compressed tissue in an direction coplanar to the at least one of the first tissue contacting surface and the second tissue contacting surface, and an applied voltage of the energy applicator not exceeding about 100 V(rms)/mm with respect to the offset electrode spacing between the electrodes.

26. Apparatus in accordance with claim 25, wherein the energy applicator includes a set of jaws.

27. Apparatus in accordance with claim 25, further comprising a pressure controller in operable connection with the set of jaws, wherein the pressure controller has a low pressure setting and a high pressure setting, wherein the low pressure setting is configured to allow the jaws to apply a low amount of pressure so as to grasp and approximate tissue without excessive damage to the tissue, and wherein the high pressure setting is configured to allow the jaws to apply a high amount of pressure so as to clamp the tissue for welding with the energy applicator and the thermally conductive material disposed at the at least one of the first tissue contacting surface and the second tissue contacting surface.

28. Apparatus in accordance with claim 25, wherein the pressure controller is configured to allow the jaws to apply a pressure is between 5 to 10 kgf/cm2 and the pressure is distributed over substantially an entire portion of the at least one of the first tissue contacting surface and the second tissue contacting surface.

29. Apparatus in accordance with claim 25, wherein the energy applicator comprises a knife for division of the target tissue.

30. Apparatus in accordance with claim 29, wherein the knife is attached to a deployable electrode portion of a radio-frequency applicator of the energy applicator.

31. Apparatus in accordance with claim 29, wherein the knife is configured to separate the target tissue during or after RF activation.

32. A method of attaching and reinforcing tissue, the method comprising:

applying energy adjacent to tissue surfaces with an energy applicator, wherein the application of the energy is configured to generate an amount of heat within a target tissue so as to evaporate intracellular and extracellular water from a target tissue to create dried tissue; and directing contact with the target tissue heated by the energy applicator with a thermally conductive material disposed adjacent the at least one of the first tissue contacting surface and the second tissue contacting surface, and evenly distributing heat within the targeted tissue area with the thermally conductive material providing a high coefficient of thermal conductivity.

33. A method of reinforcing tissue, the method comprising:

applying energy adjacent a tissue surface with an energy applicator, wherein the application of the energy is configured to generate an amount of heat within a target tissue so as to evaporate intracellular and extracellular water from the target tissue to create dried tissue; and directing current flow through the compressed tissue in an direction coplanar to the at least one of the first tissue contacting surface and the second tissue contacting surface with electrodes of the energy applicator offset by a distance, and limiting an applied voltage of the energy applicator to not exceed about 100 V(rms)/mm with respect to the offset electrode spacing between the electrodes.

\* \* \* \* \*